(12) United States Patent
Sah et al.

(10) Patent No.: US 8,957,038 B2
(45) Date of Patent: Feb. 17, 2015

(54) TREATMENT OF NEUROLOGICAL DISORDERS

(75) Inventors: Dinah W. Y. Sah, Cambridge, MA (US);
Andrei P. Guzaev, Escondido, CA (US);
Matthew H. Adams, Zimmerman, MN (US); Pei Ge, Cambridge, MA (US);
Muthiah Manoharan, Cambridge, MA (US); Douglas Ulen Gwost, Shoreview, MN (US); Gregory Robert Stewart, Plymouth, MN (US); David Kent Stiles, Maple Grove, MN (US); Brian Dale Nelson, Birchwood, MN (US); William Frederick Kaemmerer, Edina, MN (US); Don Marshall Gash, Lancaster, KY (US)

(73) Assignee: Medtronic, Inc., Minneapolis, MN (US)

( * ) Notice: Subject to any disclaimer, the term of this patent is extended or adjusted under 35 U.S.C. 154(b) by 122 days.

(21) Appl. No.: 13/383,560

(22) PCT Filed: Jul. 15, 2010

(86) PCT No.: PCT/US2010/042171
§ 371 (c)(1),
(2), (4) Date: Jan. 11, 2012

(87) PCT Pub. No.: WO2011/008982
PCT Pub. Date: Jan. 20, 2011

(65) Prior Publication Data
US 2012/0116360 A1 May 10, 2012

Related U.S. Application Data

(60) Provisional application No. 61/239,482, filed on Sep. 3, 2009, provisional application No. 61/225,839, filed on Jul. 15, 2009.

(51) Int. Cl.
*A61K 31/70* (2006.01)
*C07H 21/02* (2006.01)
*C07H 21/04* (2006.01)
*C12N 15/113* (2010.01)
*C12Q 1/68* (2006.01)

(52) U.S. Cl.
CPC .......... *C12N 15/113* (2013.01); *C12N 2310/14* (2013.01); *C12N 2310/315* (2013.01); *C12N 2310/321* (2013.01); *C12N 2310/346* (2013.01); *C12N 2310/3517* (2013.01); *C12N 2320/35* (2013.01)
USPC ......... 514/44 A; 435/375; 435/377; 536/23.1; 536/24.1; 536/24.5

(58) Field of Classification Search
None
See application file for complete search history.

(56) References Cited

U.S. PATENT DOCUMENTS

| | | | |
|---|---|---|---|
| 7,320,965 B2 * | 1/2008 | Sah et al. | 514/44 A |
| 7,749,978 B2 * | 7/2010 | Sah et al. | 514/44 R |
| 8,080,532 B2 * | 12/2011 | Sah et al. | 514/44 R |
| 2007/0167389 A1 | 7/2007 | Kaemmerer | |
| 2008/0039415 A1 | 2/2008 | Stewart et al. | |
| 2008/0221055 A1 * | 9/2008 | Sah et al. | 514/44 |
| 2008/0249039 A1 | 10/2008 | Elmen et al. | |

* cited by examiner

*Primary Examiner* — Sean McGarry
(74) *Attorney, Agent, or Firm* — William D. Schmidt; Sorell, Lenna & Schmidt LLP

(57) ABSTRACT

This invention provides treatment compositions as well as systems and methods of determining and administering an effective amount of treatment for a neurological disorder. The treatment composition can contain a labeled interfering RNA (iRNA) agent capable of decreasing expression of a target RNA associated with the neurological disorder. The methods of the invention include determining an effective amount of a therapeutic composition by introducing a solution containing a tracer into the brain of a mammal. The tracing solution is monitored until a target volume of distribution at steady state distribution is substantially achieved, and the rate of delivery of the therapeutic composition is determined. The therapeutic composition can then be administered at the rate determined by use of the tracing solution.

18 Claims, 16 Drawing Sheets

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthesized

<400> SEQUENCE: 1
gucacaaaga accgugcagt t                                               21

<210> SEQ ID NO 2
<211> LENGTH: 21
<212> TYPE: DNA
<213> ORGANISM: Artificial Sequence
<220> FEATURE:
<223> OTHER INFORMATION: Synthesized

<400> SEQUENCE: 2
cugcacgguu cuuugugact t                                               21

<210> SEQ ID NO 3
<211> LENGTH: 21
<212> TYPE: DNA
<213> ORGANISM: Artificial Sequence
<220> FEATURE:
<223> OTHER INFORMATION: Synthesized

<400> SEQUENCE: 3
gucacaaaga accgugcagt t                                               21

<210> SEQ ID NO 4
<211> LENGTH: 22
<212> TYPE: DNA
<213> ORGANISM: Artificial Sequence
```

```
<220> FEATURE:
<223> OTHER INFORMATION: Synthesized

<400> SEQUENCE: 4
tcugcacggu ucuuugugac tt                                              22

<210> SEQ ID NO 5
<211> LENGTH: 21
<212> TYPE: DNA
<213> ORGANISM: Artificial Sequence
<220> FEATURE:
<223> OTHER INFORMATION: Synthesized

<400> SEQUENCE: 5
cugcacgguu cuuugugact t                                               21
```

TREATMENT OF NEUROLOGICAL DISORDERS

CROSS-REFERENCE TO RELATED APPLICATIONS

This application is a 371 of International Patent Application PCT/US2010/0042171 titled "Treatment of Neurological Disorders," filed Jul. 15, 2010, which claims priority to and the benefit of U.S. Provisional Application No. 61/225,839, filed on Jul. 15, 2009, and titled "Treatment of Neurological Disorders," and U.S. Provisional Application No. 61/239,482, filed on Sep. 3, 2009, and titled "Huntington Gene Suppression System," the entire contents of which are incorporated in this disclosure by reference in their entirety.

BACKGROUND

Diseases of the central nervous system (CNS), including the brain, the brainstem, the spinal cord and peripheral nerves, often result in serious morbidity, death or impairment of mobility. Due to the presence of the blood brain barrier, many therapeutic agents can not enter the brain from the blood. Thus, in order to treat a neurological disorder, therapeutic agents must be directly injected into the brain.

It is desirable that a therapeutic agent to treat a CNS disease be delivered to the brain in a therapeutically effective amount. If too little therapeutic agent is administered, the disease will not be effectively treated. On the other hand, if too much therapeutic agent is administered, the therapeutic is wasted, a consequence which is particularly undesirable when the therapeutic agent is expensive or otherwise difficult to obtain. Therefore, it is important to monitor and determine the amount of therapeutic that is delivered to the brain. Methods for monitoring therapeutic agents acutely delivered to the CNS by convection enhanced delivery (CED) have been previously described in U.S. Pat. No. 7,371,225.

In addition, the distribution of any agent injected into the brain cannot be predicted due to the presence of multiple brain regions and anatomical difference from patient to patient or caused by the CNS disease. Therefore, the ability to effectively treat a CNS disorder with a therapeutic agent may be compromised by an inability to effectively determine the rate of delivery, as well as the inability to determine the effective amount of a therapeutic composition within and across multiple brain regions.

For the foregoing reasons, there is a need for a composition to treat a CNS disease, as well as systems and methods to determine and administer an effective amount of a therapeutic composition for treating a CNS disorder.

SUMMARY

The present invention is directed, in part, to the use of an interfering RNA (iRNA) agent for use in the treatment of a CNS disorder such as Huntington's Disease. Treatment of the disease comprises administering, preferably via a catheter, a therapeutically effective amount of a treatment composition to the brain of the human, wherein the treatment composition comprises an iRNA agent which has an antisense sequence that is substantially complementary to a huntingtin RNA such that the iRNA agent decreases protein expression by the Huntington RNA in the brain. The treatment composition can be administered at a rate of 0.033 µL/min to 166.67 µL/min.

The iRNA agent used in the invention can be an antisense strand comprising the nucleotide sequence of SEQ ID NO:2 [5' CUGCACGGUUCUUUGUGACTT 3']. Optionally, the iRNA agent can comprises at least 15 nucleotides of SEQ ID NO:2.

In another embodiment, the iRNA agent comprises an antisense strand comprising the nucleotide sequence of SEQ ID NO:2 and a sense strand containing the nucleotide sequence of SEQ ID NO:1 [5' GUCACAAAGAACCGUGCAGTT 3'].

Optionally, the iRNA agent comprises at least two chemically modified nucleotides. For example, the iRNA agent can comprise an antisense strand comprising SEQ ID NO:4 [5' TCUGcACGGUUCUUUGUGACTT 3'], or an antisense strand consisting of SEQ ID NO:5 [5' CUGcACGGUUCU-UUGUGACTT 3']. The iRNA agent can also comprise an antisense strand comprising SEQ ID NO:4 and a sense strand consisting of SEQ ID NO:3 [5' GucAcAAAGAAccGuG-cAGTT 3']. In another embodiment, the iRNA agent can comprise an antisense strand comprising SEQ ID NO:5 and a sense strand consisting of SEQ ID NO:3.

The concentration of the iRNA agent in the treatment composition is 0.1 mg/mL to 50 mg/mL. In one embodiment, the concentration of iRNA agent in the treatment composition is 0.5 mg/mL to 24 mg/mL. In yet another embodiment, the concentration of iRNA agent in the treatment composition is 2 mg/mL to 12 mg/mL.

Administration of the iRNA agent can be either continuous or intermittent. In one embodiment, the treatment composition is continuously administered at a rate of 0.03 µL/min to 2 µL/min. In another embodiment, the iRNA agent is administered at a rate of 0.05 µL/min to 1 µL/min.

In one embodiment, the intermittent administration can comprise: two or more cycles of administration, wherein one cycle is 6 hours to 10 days of continuous administration at a first rate followed by 1 day to 60 days of continuous administration at a second rate that is slower than the first rate, hereinafter referred to as the "slow rate"; two or more cycles of administration, wherein one cycle is 6 hours to 3 days of continuous administration at the first rate is followed by 3 days to 60 days of administration at the slow rate; or two or more cycles of administration, wherein one cycle is 1 to 3 days of continuous administration at the first rate followed by 4 days to 21 days of continuous administration at the slow rate. In one embodiment, the first rate is a rate of 0.3 µL/min to 2.0 µL/min and the slow rate is a rate of 0.03 µL/min to 0.5 µL/min. In yet another embodiment, the first rate is a rate of 0.30 µL/min to 1 µL/min and the slow rate is 0.05 µL/min to 0.3 µL/min. In another embodiment, the first rate is 0.5 µL/min and the slow rate is 0.1 µL/min.

In another embodiment, the concentration of the iRNA agent in the treatment composition is 4 mg/mL to 12 mg/mL and is administered continuously at a rate of 0.03 µL/min to 2.0 µL/min for 2 or more days.

It is contemplated that the treatment composition can be administered to neural cells, such as cortical cells, striatal cells, substantia nigra cells, and thalamus cells. The striatal cells can be selected from the group comprising putamen cells and caudate cells.

The present invention is also directed, in part, to a system useful in determining an effective amount of a therapeutic composition comprising an iRNA agent for treating a CNS disorder in a mammal. The system comprises a catheter configured to be placed in the brain of a mammal, and a tracing composition comprising an iRNA agent labeled with a detectable label. The iRNA agent can comprise an antisense sequence that is substantially complementary to a target RNA in the brain so that the labeled iRNA agent is capable of decreasing expression of the target RNA in the brain. The labeled iRNA agent also comprises a detectable label that does not adversely affect the effectiveness or distribution of the labeled iRNA agent to decrease expression of the target RNA as compared to the labeled iRNA agent without the label. The detectable label can be carbon-14. When the CNS disorder is Huntington's disease, the target RNA is a huntingtin RNA.

The catheter of the system can be implanted so as to deliver the tracing composition to regions of the brain and central nervous system by infusion methods such as intrathecal, intraparenchymal, intrastriatal, intraputamenal, intracaudate, intracerebroventricular, and intracortical infusion.

In one embodiment, the system can also contain an infusion pump operably connected to the catheter that pumps the tracing composition through the catheter to the brain and a controller for controlling the rate at which the tracing composition is delivered to the patient.

In another embodiment, the infusion pump can include a reservoir containing the tracing composition. It is contemplated that the pump can be implantable and the reservoir can be refillable.

In another embodiment, the system can contain means for monitoring the distribution of the tracing composition during delivery by imaging the detectable label to determine whether a target volume of distribution at steady state is substantially achieved.

The present invention is also directed, in part, to a method of determining and delivering an effective amount of a therapeutic composition containing a therapeutic agent via a catheter to the brain of a mammal comprising the steps of: a) introducing a solution comprising a tracer via the catheter to the brain; b) monitoring distribution of the solution during delivery by imaging the tracer in the solution to determine whether a target volue of distribution at steady state is substantially achieved; c) if target volume of distribution at steady state is not substantially achieved, modifying the rate of delivery of the solution or the concentration of the tracer in the solution or both, until target volume of distribution at steady state is substantially achieved; d) determining a rate of delivery of the therapeutic composition and the concentration of the therapeutic agent in the therapeutic composition to substantially achieve target volume of distribution at steady state based on the rate of delivery and concentration of tracer resulting in the target volume of distribution at steady state being substantially achieved in step (b) or step (c); and e) delivering the therapeutic composition at the rate determined in step (d) with the concentration of therapeutic agent in the therapeutic composition determined in step (d) via the catheter to the brain of the mammal. In one embodiment, the step of monitoring the distribution of the solution and the tracer comprises imaging the brain of said mammal one or more times using one or more imaging means from the group consisting of magnetic resonance imaging (MRI) and X-ray based imaging. In yet another embodiment, the tracer comprises an iRNA agent labeled with a detectable label. The iRNA agent can comprise an antisense sequence that is substantially complementary to a target RNA in the brain so that the labeled iRNA agent is capable of decreasing expression of the target RNA in the brain. The detectable label is chosen so that it does not adversely affect the effectiveness or distribution of the labeled iRNA agent to decrease expression of the target RNA as compared to the labeled iRNA agent without the label.

DRAWINGS

These and other features, aspects, and advantages of the present invention will become better understood with regard to the following description, appended claims, and accompanying drawings where:

Figure 4:
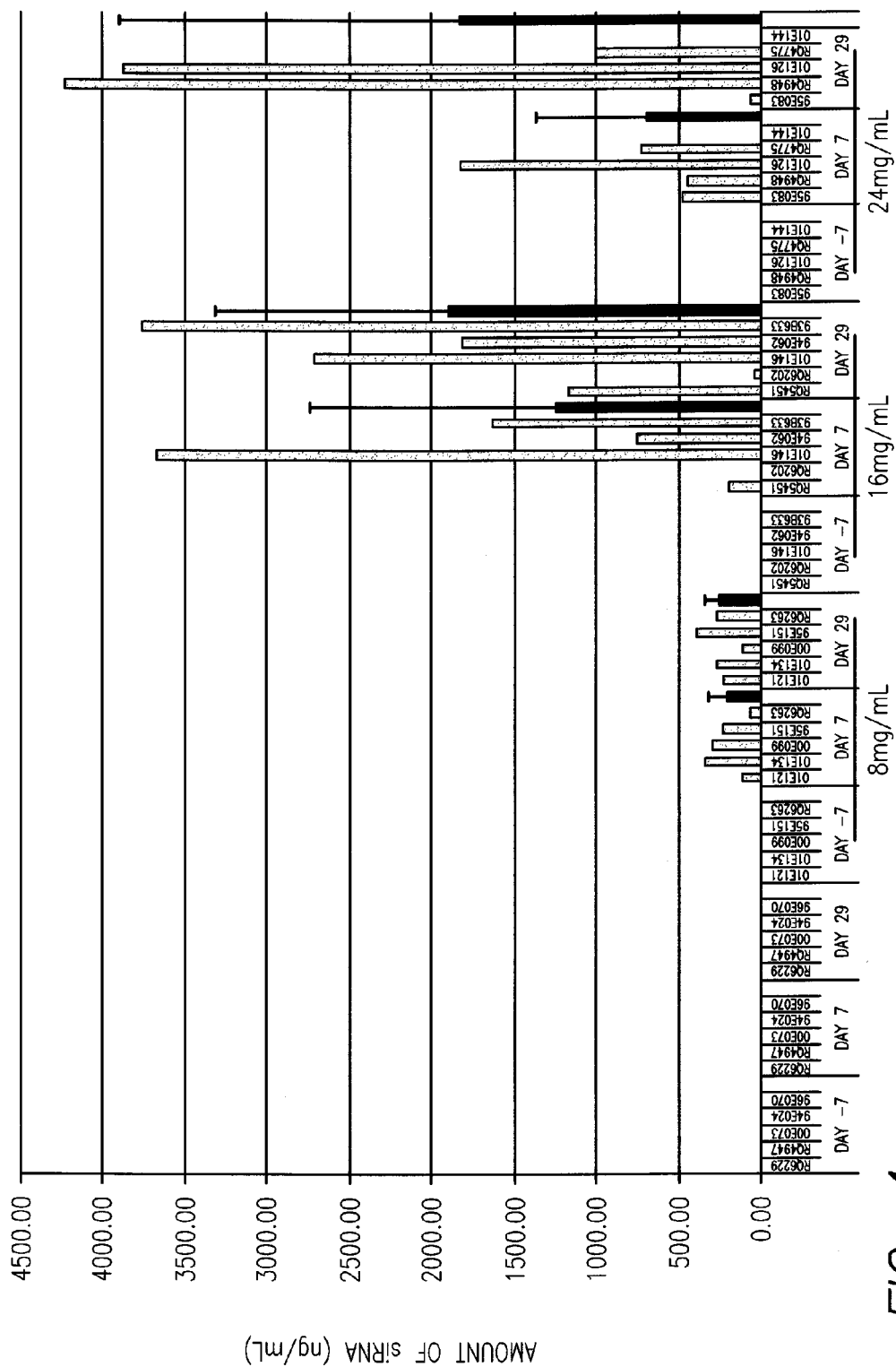

FIG. 4 shows a graph depicting the amount of detectable siRNA in the CSF of non-human primates 7 days before the start of infusion, after 7 days of continuous infusion, and after 29 days of continuous infusion with 0, 8 mg/mL, 16 mg/mL, or 24 mg/mL AD-5997 siRNA.

Figure 5:
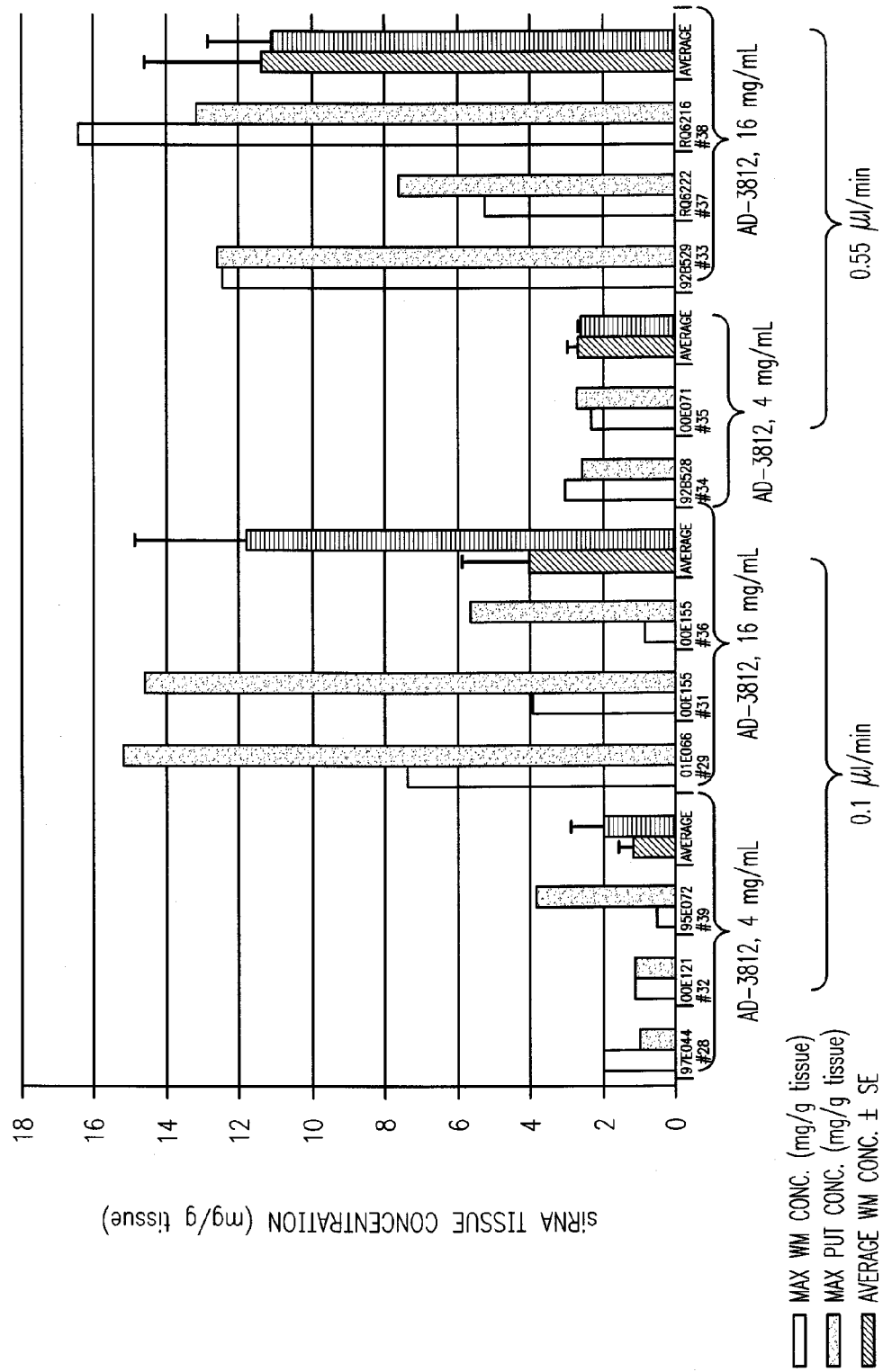

FIG. 5 shows a graph depicting the tissue concentration of AD-3812 siRNA in non-human primates after 7 days of intraputamenal infusion with flow rates of 0.1 µL/min or 0.55 µL/min and AD-3812 siRNA concentrations of 4 mg/mL or 16 mg/mL.

Figure 6:
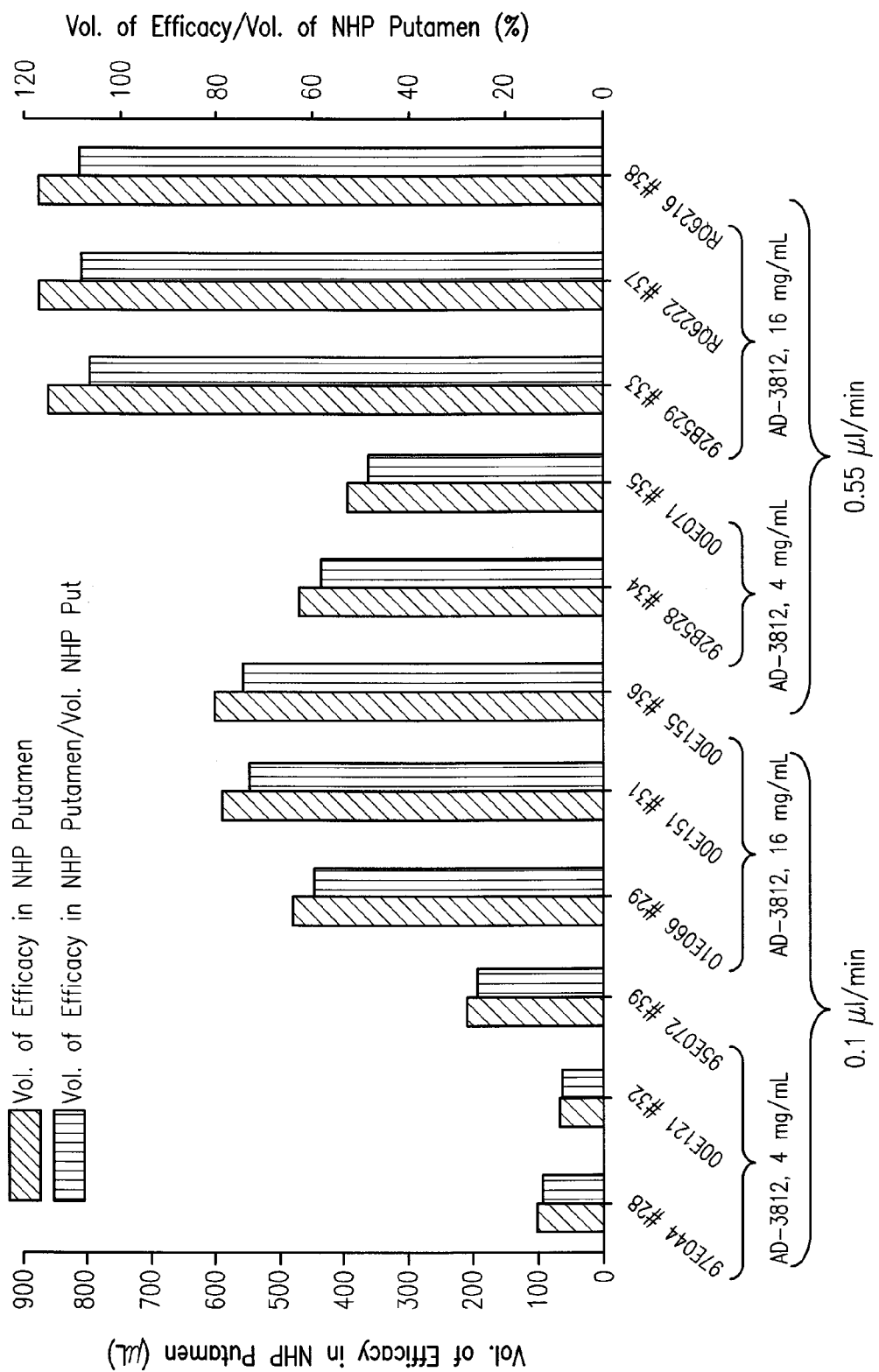

FIG. 6 shows a graph depicting the volume of efficacy of AD-3812 siRNA suppression in non-human primate putamen compared to the volume of non-human primate putamen with a concentration of AD-3812 siRNA of 4 mg/mL or 16 mg/mL and flow rates of 0.1 µL/min (left side of graph) or 0.55 µL/min (right side of graph).

FIG. 7 shows a graph depicting the suppression of target mRNA normalized to PBS in the putamen of non-human primates after 7 days of infusion with 0, 12 mg/mL, or 8 mg/mL of AD-3812 siRNA.

Figure 7A:
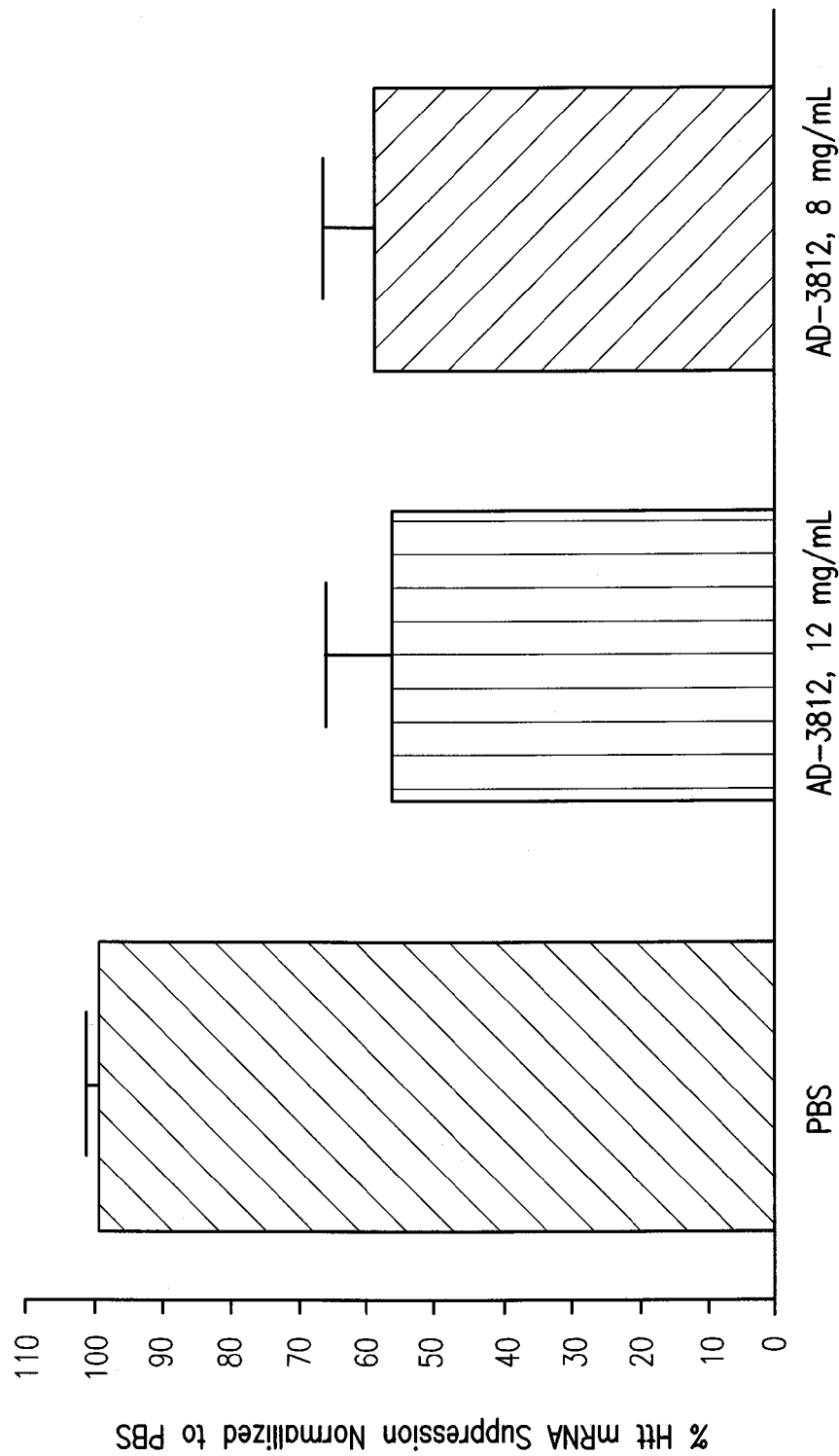
Figure 7B:
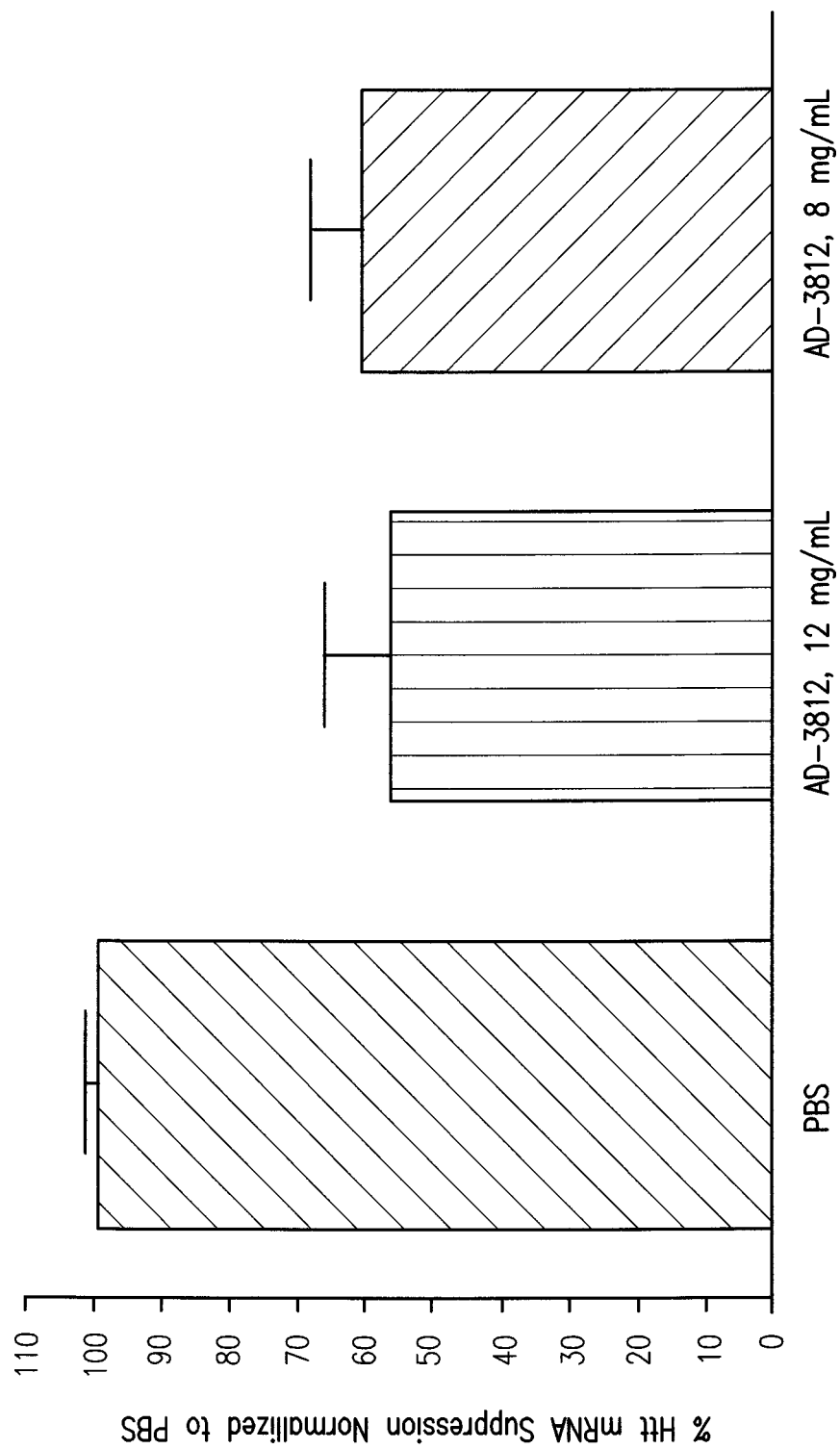

FIG. 7A depicts the target mRNA suppression as measured 0-2 mm from the infusion site. FIG. 7B depicts the target mRNA suppression as measured 4 mm from the infusion site.

Figure 8:
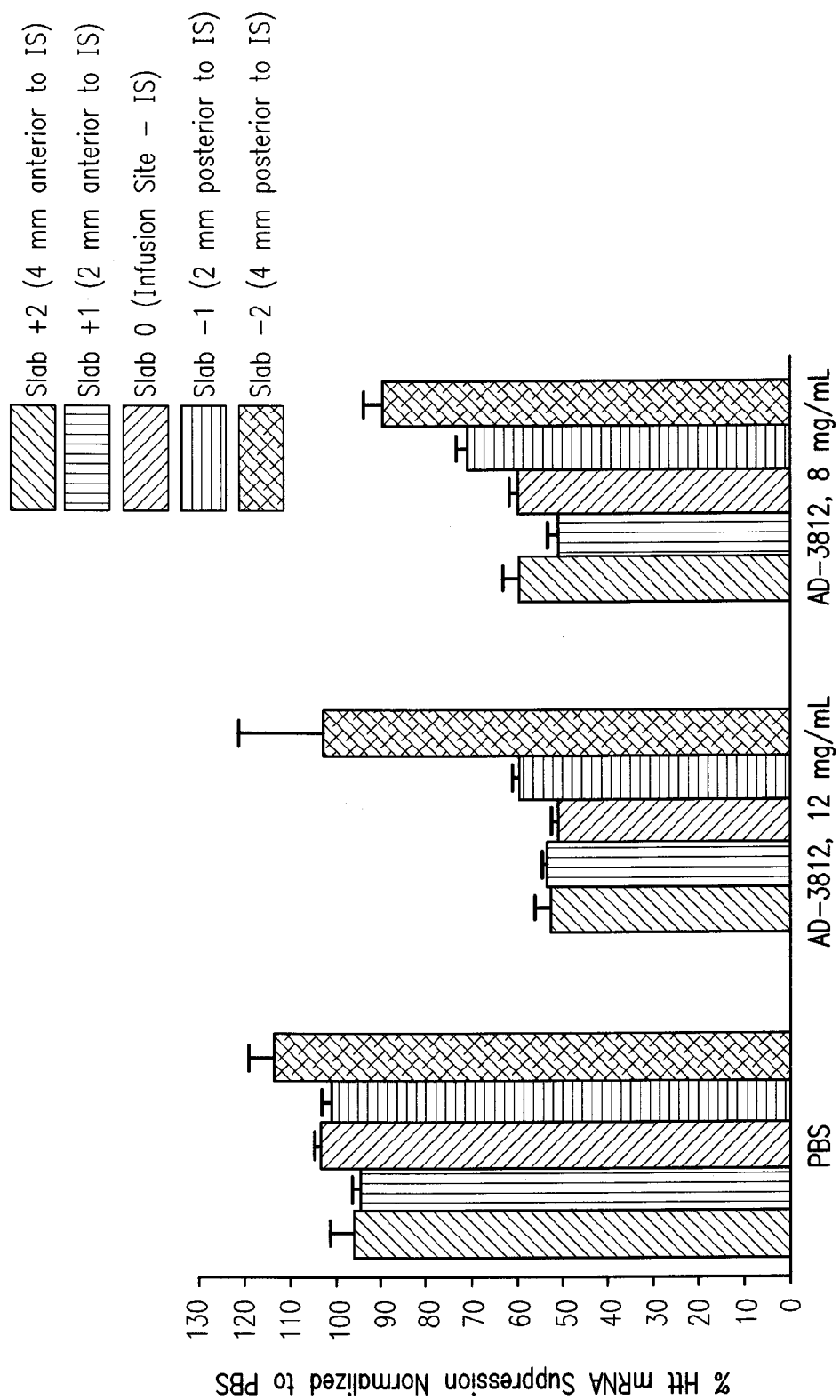

FIG. 8 shows a graph depicting the suppression of target mRNA normalized to PBS and the anterior-posterior location of the suppression in the putamen of non-human primates after 7 days of infusion with 0, 12 mg/mL, or 8 mg/mL of AD-3812 siRNA.

Figure 9A:
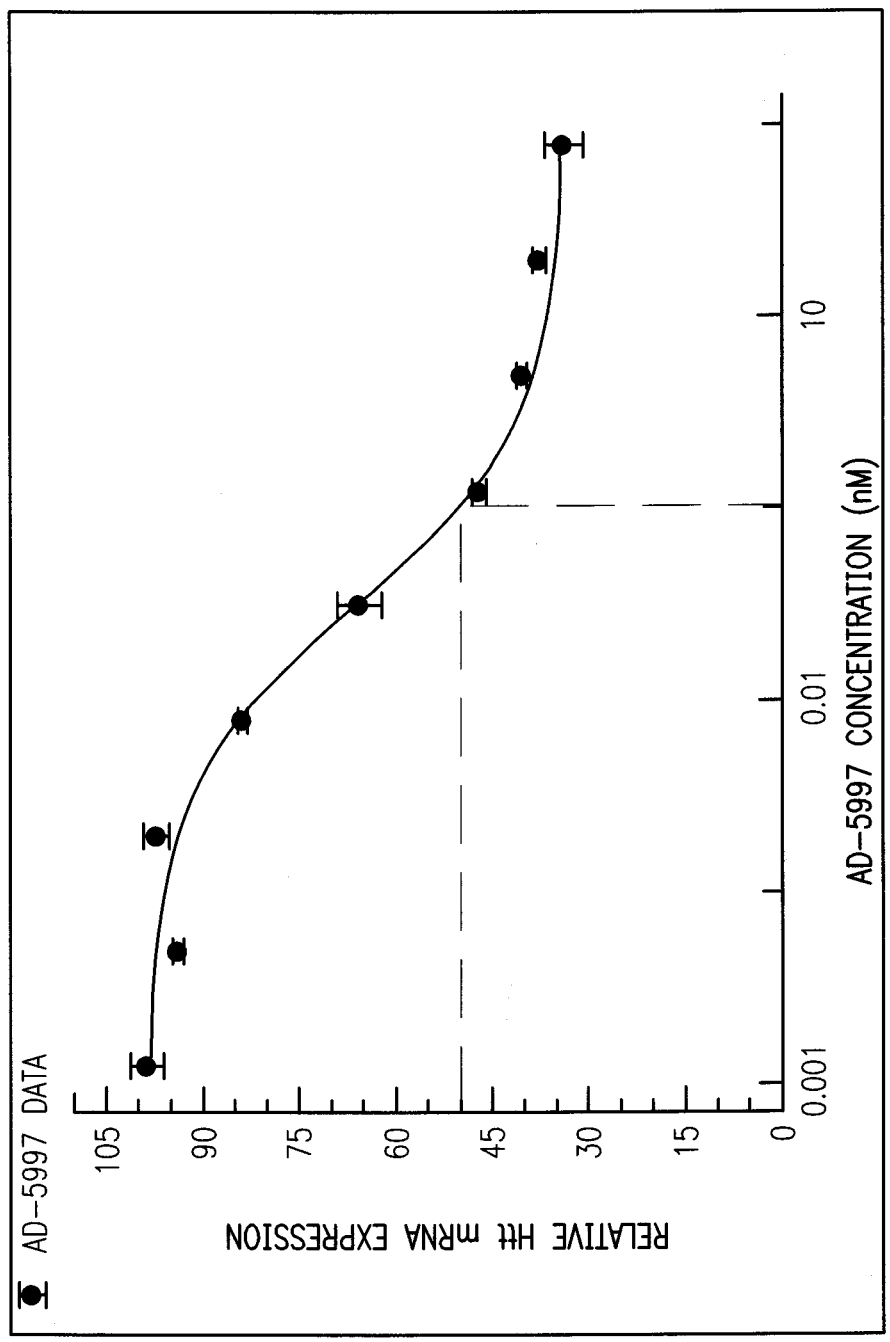
Figure 9B:
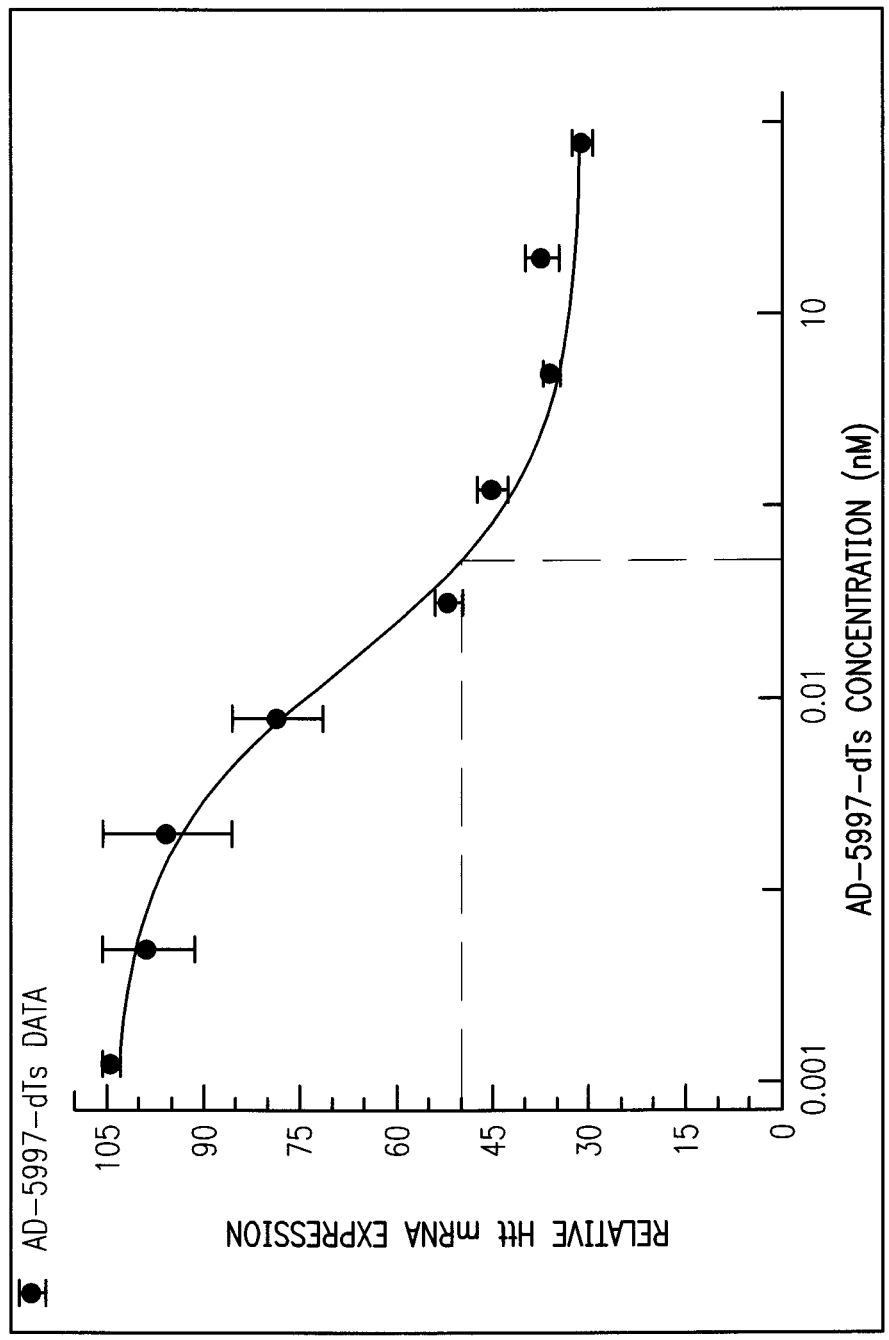

FIG. 9A shows a graph depicting the suppression of target mRNA using increasing concentrations of AD-5997. FIG. 9B shows a graph depicting the suppression of target mRNA using increasing concentrations of AD-5997-dTs.

Figure 10:
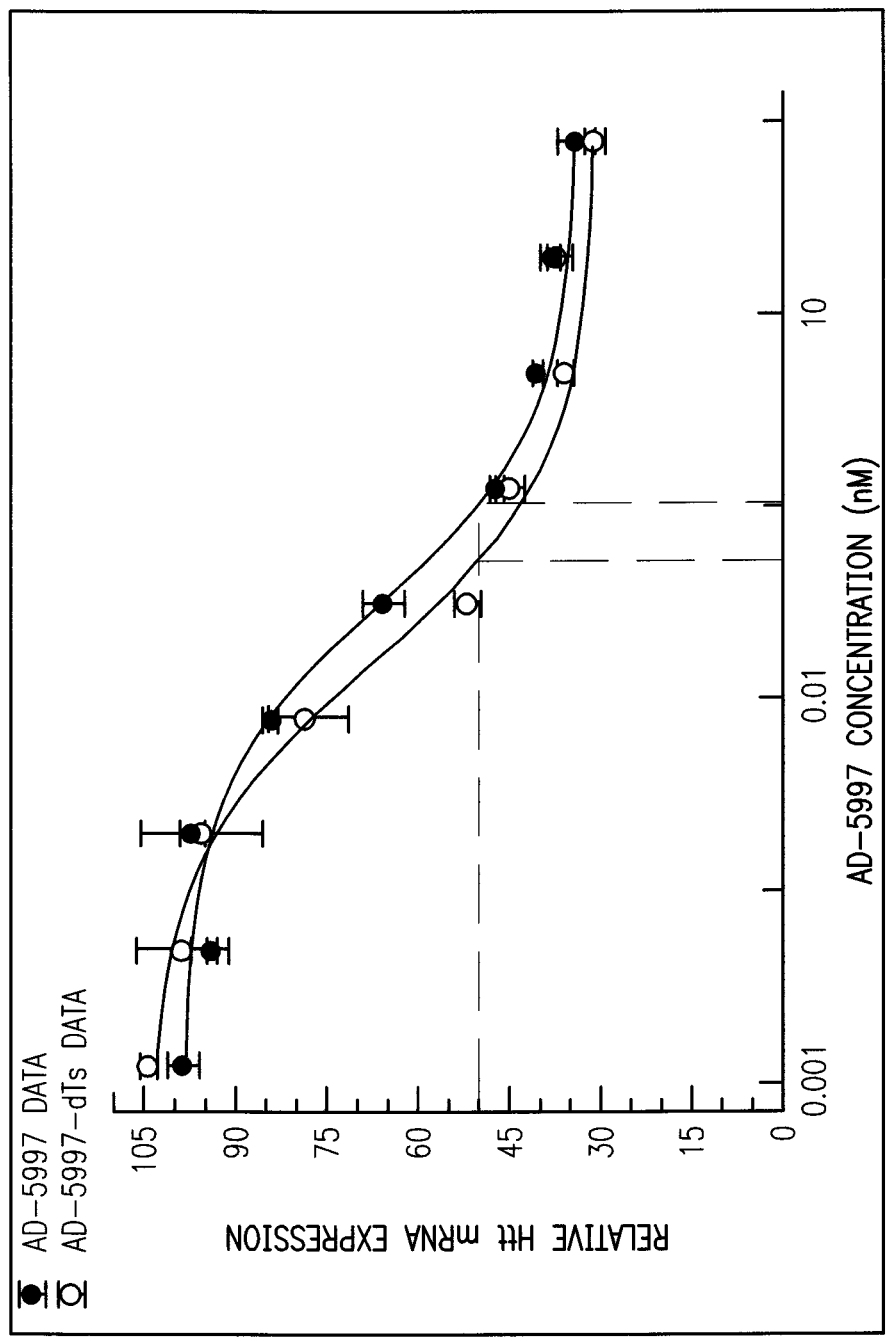

FIG. 10 shows one graph depicting the suppression of target mRNA using increasing concentrations of AD-5997 and using increasing concentrations of AD-5997-dTs.

Figure 11:
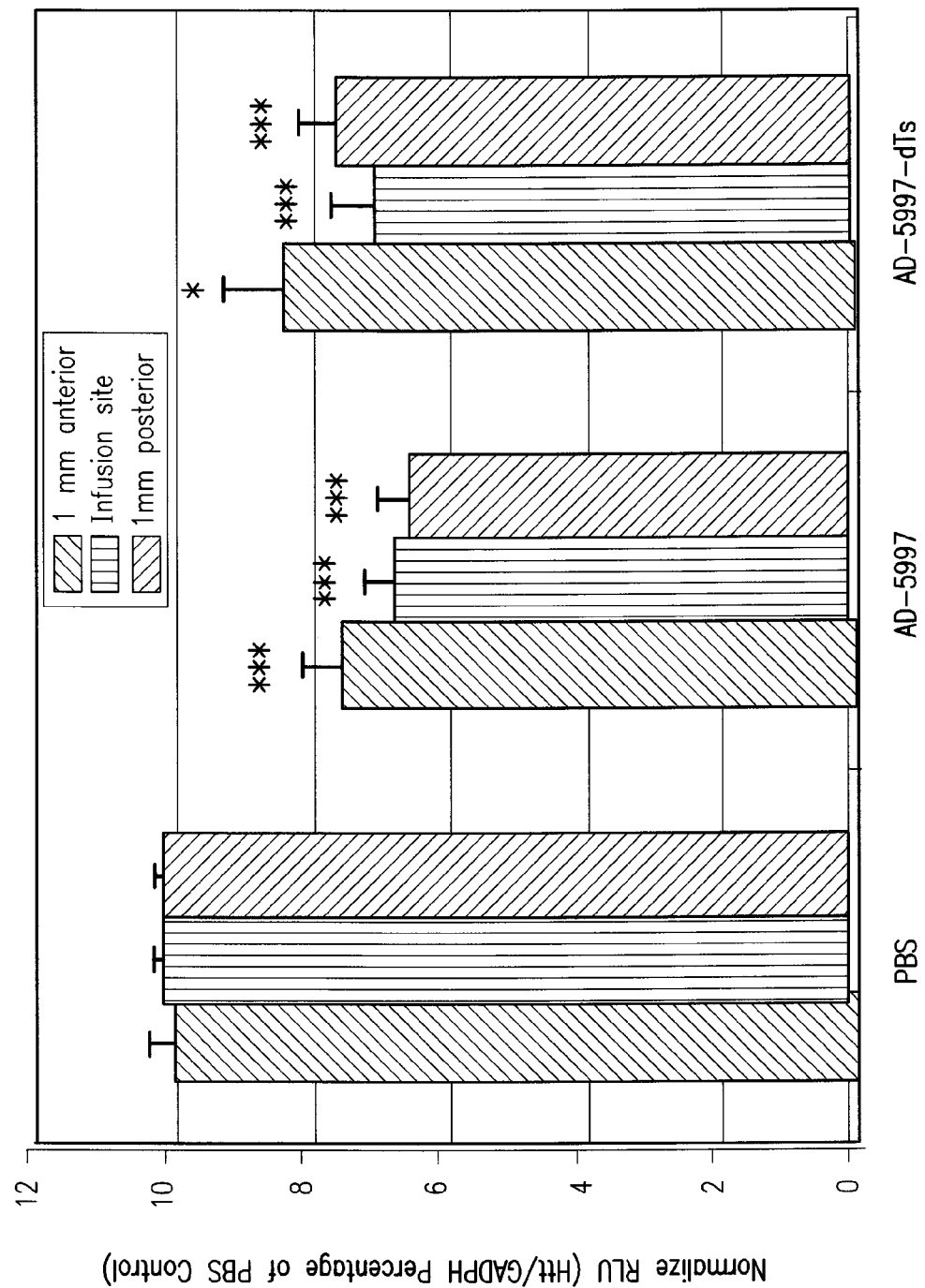

FIG. 11 shows a graph depicting the suppression of Htt target mRNA in vivo with AD-5997 or AD-5997-dTs. *p<0.01, ***p<0.001, vs PBS (ANOVA, Bonferroni post-test).

Figure 12:
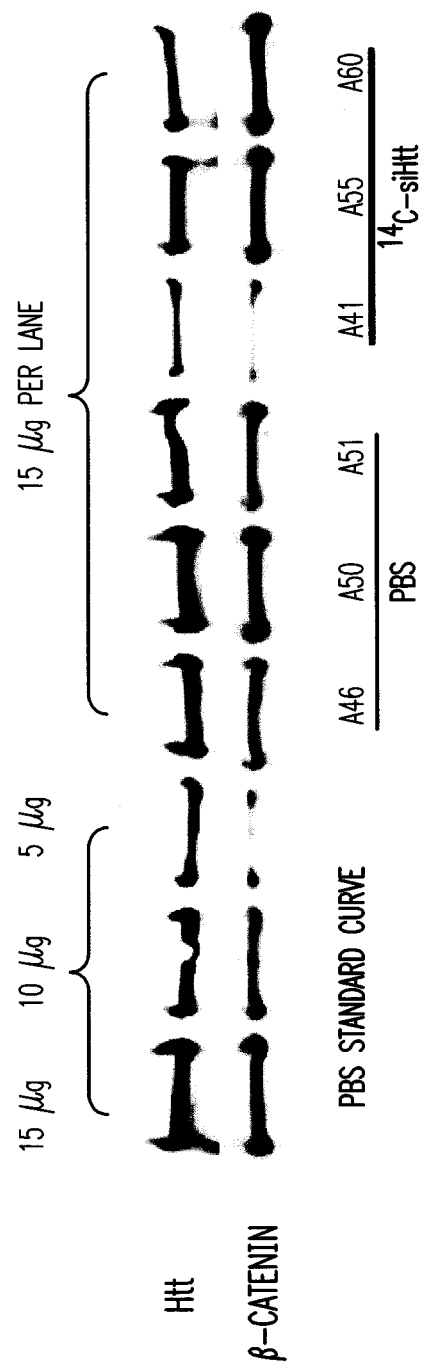

FIG. 12 shows a western blot depicting the suppression of Htt protein in tissue punches from non-human primate putamen.

Figure 13:
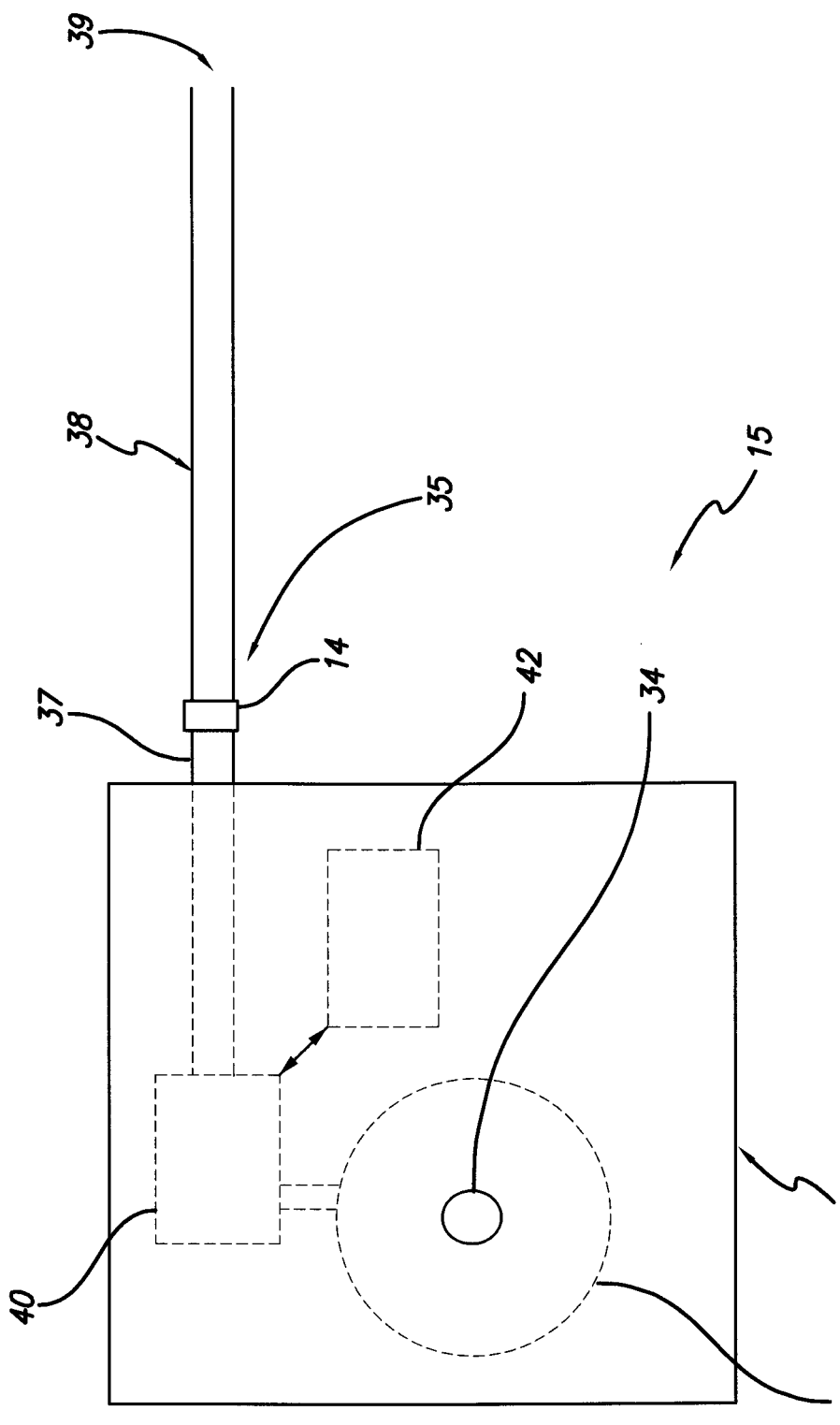

FIG. 13 shows a diagrammatic illustration of a system for delivering a solution to a mammal according to an embodiment of the invention.

Figure 14:
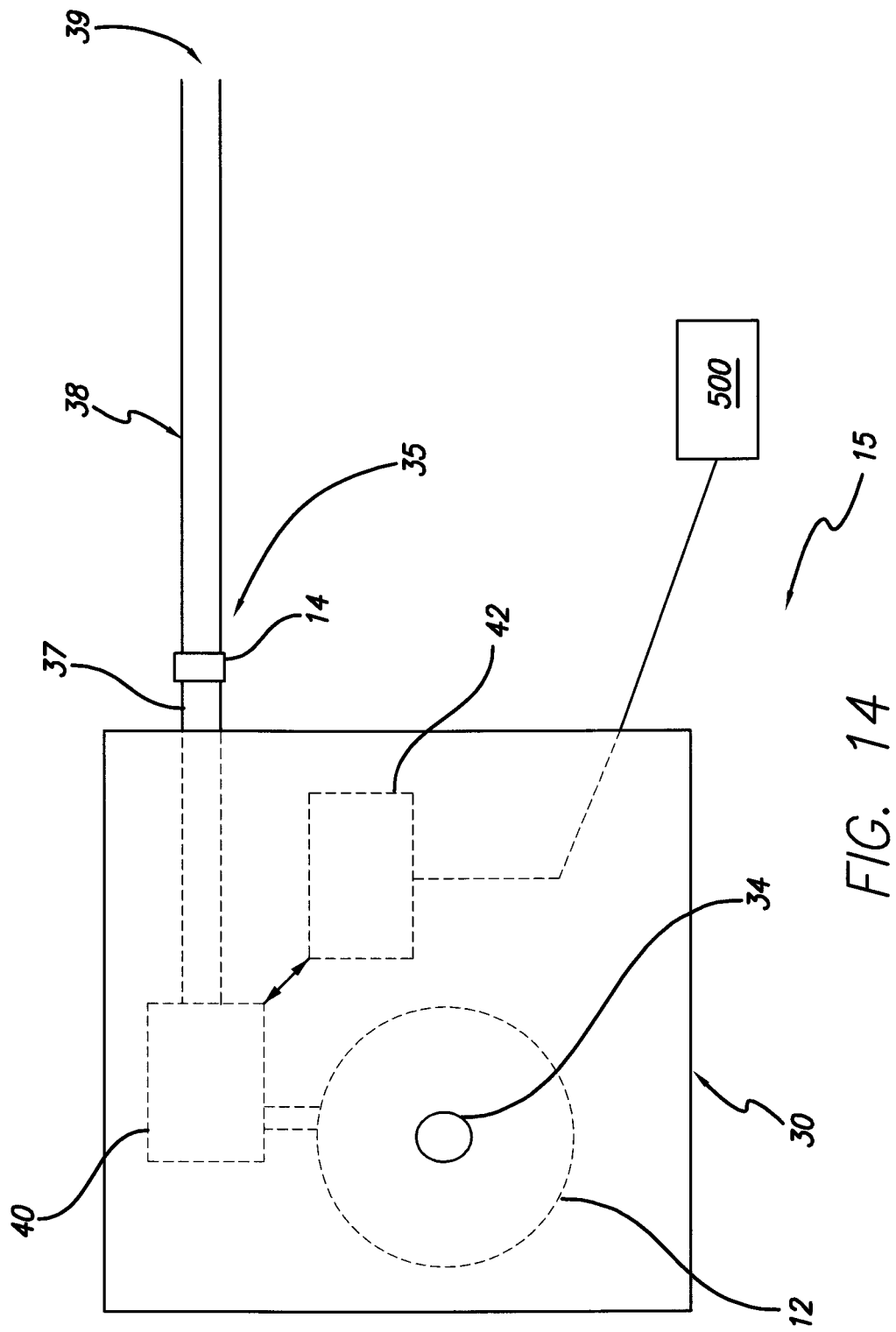

FIG. 14 shows a diagrammatic illustration of a system for delivering a solution to a mammal according to another embodiment of the invention.

DESCRIPTION

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides. This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other. However, where a first sequence is referred to as "substantially complementary" with respect to a second sequence, the two sequences can be fully complementary, or they may form one or more mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may be referred to as "fully complementary." "Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use. As used herein, a polynucleotide which is "substantially complementary to at least part of" a messenger RNA (mRNA) refers to a polynucleotide which is substantially complementary to a contiguous portion of the mRNA of interest, for example, an mRNA encoding Huntingtin. For example, a polynucleotide is complementary to at least a part of a Huntingtin mRNA if the sequence is substantially complementary to a non-interrupted portion of an mRNA encoding Huntingtin.

As used herein, the term "comprise" and variations of the term, such as "comprising" and "comprises," are not intended to exclude other additives, components, integers or steps.

"Expression" of a nucleotide sequence refers to the transcription of the nucleotide sequence and its subsequent translation into a polypeptide.

"G," "C," "A," "T" and "U" each generally stand for a nucleotide that contains guanine, cytosine, adenine, thymine, and uracil as a base, respectively. One of skill in the art is well aware that guanine, cytosine, adenine, thymine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. As used herein, "unmodified" or "natural" nucleobases include the purine bases adenine (A) and guanine (G), and the pyrimidine bases thymine (T), cytosine (C), and uracil (U). "Modified" nucleobases include other synthetic and natural nucleobases, such as 2'-O-methyladenosine-5'-phosphate, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

By "Huntingtin protein" or "Htt protein" as used herein refers to any Huntingtin protein, peptide, or polypeptide associated with the development or maintenance of Huntington disease (HD). The terms "huntingtin" and "htt" refer to nucleic acid sequences encoding any Huntingtin protein, peptide, or polypeptide, such as huntingtin RNA or huntingtin DNA (Van Dellen and Hannon, 2004, *Neurogenetics,* 5(1):9-17). The GeneBank accession number for the *Homo sapiens* huntingtin (htt) mRNA is NM_002111.

The term "label" refers to any detectable molecule. For example, a label can be an isotope such as carbon-11, carbon-14, fluorine-18, iodine-131, indium-111, and gadolinium.

The term "mammal" is defined as an individual belonging to the class Mammalia and includes, without limitation, humans, domestic and farm animals, and zoo, sports, and pet animals, such as cows, sheep, dogs, horses, cats and cows.

"Monitoring" refers to obtaining serial images of a therapeutic composition containing a tracer or label as it spreads within a tissue. By monitoring the spread of a tracer, the location and volume of distribution of the tracer solution within a tissue may be determined at any time during the infusion process. Serial images may be obtained at any rate up to the maximum rate that the imaging instrument can obtain images. For example, serial images may be obtained at intervals ranging from a few minutes to hours, but more typically at intervals of minutes, such as intervals of 1, 2, 5, 10, 15, 20 or 30 minutes. The interval between serial images may be varied during infusion. In some instances, it may be desirable to obtain images at short intervals (for example, every 5, 10, or 15 seconds) at the beginning of the infusion process to detect backflow along the catheter, or to verify that the infusate is entering the desired target tissue. Once delivery to the proper site is confirmed, the interval between images may be lengthened, and the images used to follow the progress of infusion, for example, to determine if solution is reaching the targeted tissue, tissue outside of the targeted area, or if the desired steady state delivery of the solution has been reached.

The terms "sense strand" or "sense sequence" refers to the strand of a dsRNA that includes a region that is substantially complementary to a region of the antisense strand. The terms "antisense strand" or "antisense sequence" refers to the strand of a dsRNA which includes a region that is substantially complementary to a target sequence.

The terms "silence," "suppression," "knockdown," and "inhibit the expression of," in as far as they refer to the target gene, refer to at least partial suppression of the expression of the target gene, as manifested by a reduction of the amount of mRNA which may be isolated from or detected in a first cell or group of cells in which the target gene is transcribed and which has been treated such that the expression of the target gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} * 100\%$$

Alternatively, the degree of inhibition may be given in terms of a reduction of a parameter that is functionally linked to target gene transcription, e.g. the amount of protein encoded by the target gene that is secreted by a cell, or the number of cells displaying a certain phenotype, e.g. apoptosis. In principle, target gene silencing may be determined in any cell expressing the target, either constitutively or by genomic engineering, and by any appropriate assay. For example, in certain instances, expression of the target gene is suppressed by 5 to 100% by administration of the iRNA agent.

The term "solution" refers to a composition comprising a solvent and a solute, and includes true solutions and suspensions. Examples of solutions include a solid, liquid or gas dissolved in a liquid and particulates or micelles suspended in a liquid.

As used herein, "target RNA" or "target sequence" refers to a contiguous portion of the nucleotide sequence of an mRNA molecule formed during the transcription of a gene, including mRNA that is a product of RNA processing of a primary transcription product.

The phrase "target volume of distribution at steady state" refers to a desired volume of tissue, such as brain tissue, receiving a solution containing a chemical moiety, where the solution has reached equilibrium inside the tissue, where the rate of delivery of the solution is equal to the rate of clearance of the solution. If a solution has reached the target volume of distribution at steady state, then the observed behavior of the solution remains constant. The target volume of distribution at steady state is not achieved until some time has elapsed after delivery of the solution is started or initiated.

A "therapeutic composition" or "treatment composition" means a substance that is intended to have a therapeutic effect such as pharmaceutical compositions, genetic materials, biologics, and other substances. Pharmaceutical compositions may be configured to function in an implanted environment with characteristics such as stability at body temperature to retain therapeutic qualities, concentration to reduce the frequency of replenishment, and the like. Genetic materials include substances intended to have a direct or indirect genetic therapeutic effect such as genetic vectors, genetic regulator elements, genetic structural elements, DNA, iRNA and the like. Biologics include substances that are living matter or derived from living matter intended to have a therapeutic effect such as stem cells, platelets, hormones, biologically produced chemicals, and the like.

A "therapeutically effective amount" is an amount of the therapeutic or treatment composition that provides a therapeutic benefit in the treatment, prevention, or management of a CNS disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by ordinary medical practitioner, and may vary depending on factors known in the art, such as, e.g. the type of disease, the patient's history and age, the stage of disease, and the administration of other therapeutic agents.

The term "tracer" refers to a substance that is detectable by imaging techniques, such as, for example, sonic techniques, or magnetic resonance- or X-ray-based imaging, for example, magnetic resonance imaging (MRI) or computed tomography (CT). In some instances, the tracer is itself a therapeutic agent. In other instances, the tracer is not a therapeutic agent. In others, the tracer is conjugated to a therapeutic agent.

Neurological Disorders

The peripheral and central nervous systems contain many different types of neural cells. A neural cell can be any cell in the nervous system, e.g., a nerve cell (i.e., a neuron), a sensory neuron or a motor neuron, or a glial cell. Exemplary neurons include dorsal root ganglia of the spinal cord, spinal motor neurons, retinal bipolar cells, cortical cells, striatal cells (including putamen cells and caudate cells), substantia nigra cells, and thalamus cells of the brain, hippocampal pyramidal cells, and purkinje cells of the cerebellum. Exemplary glial cells include oligodendrocytes and astrocytes of the central nervous system, and the Schwann cells of the peripheral nervous system.

It is contemplated that methods and compositions detailed in the present invention are used to determine and administer an effective amount of treatment for treating a neurological disorder described herein, and can be used with any dosage and/or formulation described herein, as well as with any route of administration described herein. A neurological disease or disorder is any disease or disorder that affects the nervous system (the central or peripheral nervous system). Exemplary neurological diseases and disorders include Huntington's Disease (HD), Parkinson's Disease (PD), Amyotrophic Lateral Sclerosis (ALS), Alzheimer's Disease, Lewy body dementia, Multiple System Atrophy, spinal and bulbar muscular atrophy (Kennedy's disease), Tourette Syndrome, Autosomal dominant spinocerebellar ataxia (SCA) (e.g., Type 1 SCA1, Type 2 SCA2, Type 3 (Machado-Joseph disease) SCA3/MJD, Type 6 SCA6, Type 7 SCAT, Type 8 SCAB), Friedreich's Ataxia and Dentatorubral pallidoluysian atrophy (DRPLA/Haw-River syndrome), myotonic dystrophy (DM1 and DM2), schizophrenia, age associated memory impairment, autism, attention-deficit disorder, and bipolar disorder.

Huntington's disease (HD) is an autosomal dominant genetic disorder that causes neurodegenerative disease characterized by involuntary movement, dementia, and behavioral changes, usually beginning in middle age (35 to 50 years). Symptoms and signs of HD develop insidiously. Anhedonia or asocial behavior may be the first behavioral manifestation. Dementia or psychiatric disturbances, ranging from apathy and irritability to full-blown bipolar or schizophreniform disorder, may precede the movement disorder or develop during its course. Motor manifestations include flicking movements of the extremities, a lilting gait, motor impersistence (inability to sustain a motor act, such as tongue protrusion), facial grimacing, ataxia, and dystonia. The caudate nucleus atrophies, the small-cell population degenerates, and levels of the neurotransmitters gamma-aminobutyric acid (GABA) and substance P decrease. This degeneration results in characteristic "boxcar ventricles" seen on computed tomography (CT) scans.

The gene involved in Huntington's disease (IT-15) is located at the end of the short arm of chromosome 4. The underlying cause of HD is a gain of function mutation in the gene encoding huntingtin (htt). A mutation occurs in the coding region of this gene and produces an unstable expanded trinucleotide repeat (cytosine-adenosine-guanosine), resulting in a protein with an expanded glutamate sequence. The Huntingtin gene product is expressed at similar levels in patients and controls, and the genetics of the disorder suggest that the expansion of the polyglutamine repeat induces a toxic gain of function, perhaps through interactions with other cellular proteins. As such, suppression of htt expression may provide an effective treatment for this disease.

Treatment for Huntington's disease beyond symptom management is currently not available. The choreic movements may be treated with tetrabenazine, and agitated behaviors may be partially suppressed by treatment with antipsychotics (e.g., chlorpromazine or haloperidol) or reserpine until adverse effects of lethargy, hypotension, or parkinsonism occur.

Interfering RNA

Double-stranded RNA molecules (dsRNA) have been shown to block gene expression in a highly conserved regulatory mechanism known as RNA interference. (WO 99/32619) Interfering RNAs (iRNAs), or small interfering RNAs (siRNAs) are synthetic, double-stranded oligoribonucleotides that harness RNA interference. iRNAs selectively degrade endogenous or pathogenic target RNA and reduce levels of the corresponding protein. An iRNA agent may act by one or more of a number of mechanisms, including post-transcriptional cleavage of a target mRNA, or pre-transcriptional or pre-translational mechanisms. This natural mechanism has become the focus for the development of a class of pharmaceutical agents for treating disorders that are caused by the aberrant regulation of a gene or the expression of a mutant form of a gene.

The use of iRNA agents to treat neurological disorders, for example, HD, has been described previously. (U.S. Pat. No. 7,320,965) The delivery of iRNA agents to treat HD by local delivery of an iRNA agent and subsequent retrograde transport away from the site of administration has been shown. (U.S. 2008/0039415)

iRNA agents used in the present invention can be any RNA agent that can decrease the expression of a target gene, preferably an endogenous or pathogen target RNA expressed in the brain of a mammal. In one embodiment, the method of the invention contemplates that the iRNA agent is an antisense RNA strand, or a double stranded RNA duplex. The iRNA duplex has an antisense strand complementary to a nucleotide sequence of the target nucleic acid, and a sense strand sufficiently complementary to hybridize to the antisense strand.

The methods of the present invention contemplate an iRNA agent than can target a nucleic acid, e.g., a huntingtin (htt) RNA, involved in the pathogenesis of a neurological disorder, or target a polymorphism or mutation of the nucleic acid. Additionally, the iRNA agent can target a sequence in a codon of the open reading frame, the 3'UTR or the 5'UTR of the mRNA transcript of the gene involved in the neurological disorder. The iRNA agent can target a spliced isoform of mRNA. It is also contemplated that the iRNA agent can target a nucleic acid that encodes a polypeptide known to interact with the Huntingtin protein. For example, the iRNA agent can target a nucleic acid encoding the Huntington-associated protein-1 (HAP-1).

Individuals having a particular genotype are candidates for treatment with an iRNA agent of the invention. For example, individuals who would benefit from treatment carry a particular genetic mutation which places them at increased risk for developing a neurological disorder, e.g., HD. An individual carrying a CAG trinucleotide expansion in the htt gene (e.g., more than 36 repeats) is at increased risk for developing HD and is a candidate for treatment with an iRNA agent featured in the invention. In addition, a single-nucleotide polymorphism (SNP) in the htt gene has been found to be an indicator of the presence of the expanded CAG repeat that triggers HD, and as such, a human carrying this SNP may be a candidate for treatment with an iRNA agent targeting htt.

One aspect of the invention relates to a method of treating or preventing a neurological disorder, for example, a CNS disorder, by treating a subject having, or at risk for developing, a neurological disorder by administering an iRNA agent that inhibits expression of a target RNA levels in the brain of a mammal. In one embodiment, the target RNA is huntingtin (htt) RNA.

In one embodiment, the iRNA agent can inhibit, or decrease, htt RNA, thereby inhibiting production of Huntingtin protein in a human having or at risk for developing HD.

The invention provides a method for treating the brain of a subject with HD or at risk of developing HD with a treatment composition. In this embodiment, the treatment composition contains an iRNA agent with an antisense sequence that is substantially complementary to a huntingtin RNA in the brain such that the iRNA agent decreases protein expression by the huntingtin RNA. In another embodiment, the treatment composition contains an iRNA agent with an antisense sequence that is substantially complementary to a huntingtin RNA in the brain such that the iRNA agent reduces expression of the Huntingtin protein.

The sequence of the iRNA used in the methods of the invention can be determined from a nucleotide sequence of at least 15 nucleotides long from a target mRNA, e.g., an htt mRNA, and synthesizing the iRNA agent. The sense strand of the iRNA agent includes the nucleotide sequence selected from the target RNA, and the antisense strand is sufficiently complementary to hybridize to the sense strand.

The iRNA agent used in the methods of the invention when Huntington's disease is the CNS disorder can be a sense strand comprising SEQ ID NO:1 [5' GUCACAAAGAAC-CGUGCAGTT 3'] and an antisense strand comprising SEQ ID NO:2 [5'CUGCACGGUUCUUUGUGACTT 3']. Optionally, the iRNA agent can comprises 15 nucleotides or more nucleotides of SEQ ID NO:2. For example, the iRNA agent comprises the nucleotide sequence of SEQ ID NO:2.

The iRNA agent of the invention may be synthesized and/or modified by methods well established in the art, such as those described in "Current protocols in nucleic acid chemistry," Beaucage, et al. (Edrs.), John Wiley & Sons, Inc., New York, N.Y., USA. For example, the dsRNA used in the iRNA agents of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. Use of similar techniques to prepare other oligonucleotides, such as the phosphorothioates and alkylated derivatives, are also known in the art.

The iRNA agents can be administered in isolated form, or can be part of a treatment used for the methods described herein, particularly as a treatment composition formulated for delivery to a brain or formulated for intracranial infusion. The treatment compositions can contain one or more iRNA agents.

The oligonucleotides employed in the iRNA agents of the invention may additionally or alternatively comprise nucleobase modifications or substitutions. The iRNA agent may include a modification that improves the stability or distribution of the iRNA agent in a brain, such as, for example, addition of one or more terminal 5' thymidine bases. The nucleotides at one or both of the iRNA duplex may be modified to prevent or inhibit the activation of cellular enzymes, such as, for example, certain nucleases. In certain instances, conjugation of a cationic ligand to oligonucleotides often results in improved resistance to nucleases. Other techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, 1995, Nat. Med., 1:1116-8).

The iRNA agent used in the invention can be chemically modified at one or more positions. Chemical modifications may include, but are not limited to 2' modifications, introduction of non-natural bases, covalent attachment to a ligand, and replacement of phosphate linkages with thiophosphate linkages. It is not necessary for all positions in a given compound to be uniformly modified. Conversely, more than one modification may be incorporated in a single iRNA compound or even in a single nucleotide.

Additional modifications may also be made at other positions on the iRNA oligonucleotide, particularly the 3' position of the sugar on the 3' terminal nucleotide. For example, an additional modification of iRNA of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., 1989, Proc. Natl. Acad. Sci. USA, 86(17):6553-6), cholic acid (Manoharan et al., 1994, Bioorg. Med. Chem. Lett., 4:1053), a thioether, e.g., hexyl-5-tritylthiol (Manoharan et al., 1992, Ann. N.Y. Acad. Sci., 660:306-9; Manoharan et al., 1993, Bioorg. Med. Chem. Lett., 3:2765), a thiocholesterol (Oberhauser et al., 1992, Nucl. Acids Res., 20(3):533-8), an aliphatic chain, e.g., dodecandiol or undecyl residues (Saison-Behmoaras et al., 1991, EMBO J., 10(5):111-8; Kabanov et al., 1990, FEBS Lett., 259(2):327-30; Svinarchuk et al., 1993, Biochimie, 75(1-2):49-54), a phospholipid, e.g., di-hexadecyl-rac-glycerol or triethylammonium 1,2-di-O-hexadecyl-rac-glycero-3-H-phosphonate (Manoharan et al., 1995, Tetrahedron Lett., 36:3651; Shea et al., 1990, Nucl. Acids Res., 18(13):3777-83), a polyamine or a polyethylene glycol chain (Manoharan et al., 1995, Nucleosides & Nucleotides, 14:969), adamantane acetic acid (Manoharan et al., 1995, Tetrahedron Lett., 36:3651), a palmityl moiety (Mishra et al., 1995, Biochim. Biophys. Acta, 1264(2):229-37), or an octadecylamine or hexylamino-carbonyl-oxycholesterol moiety (Crooke et al., 1996, J. Pharmacol. Exp. Ther., 277(2):923-37).

Additionally, at least one nucleotide may be modified to form a locked nucleotide. Such a locked nucleotide contains a methylene bridge that connects the 2'-oxygen of ribose with the 4'-carbon of ribose. Oligonucleotides containing a locked nucleotide are described in Koshkin et al., (1998, Tetrahedron, 54:3607-30) and Obika et al. (1998, Tetrahedron Lett., 39:5401-4). Introduction of a locked nucleotide into an oligonucleotide improves the affinity for complementary sequences and increases the melting temperature by several degrees (Braasch et al., 2001, Chem. Biol., 8:1-7).

Other modifications include conjugating a ligand to an iRNA, which can enhance its cellular absorption. In certain instances, a hydrophobic ligand can be conjugated to the dsRNA to facilitate direct permeation of the cellular membrane. Alternatively, the ligand conjugated to the iRNA is a substrate for receptor-mediated endocytosis.

Optionally, the iRNA agent comprises at least two chemically modified nucleotides. For example, the iRNA agent can comprise a sense strand consisting of SEQ ID NO:3 [5' GucAcAAAGAAccGuGcAGTT 3'] and an antisense strand consisting of SEQ ID NO:4 [5' TCUGcACGGUUCUUU-GUGACTT 3']; or the iRNA agent comprises a sense strand consisting of SEQ ID NO:3 [5' GucAcAAAGAAccGuG-cAGTT 3'] and an antisense strand consisting of SEQ ID NO:5 [5' CUGcACGGUUCUUUGUGACTT 3']. Capital letters represent unmodified nucleotide bases, the lower case letters represent 2'-O-methyl modifications. For example, "u" represents a 2'-O-methyluracil-5'-phosphate modified nucleotide base, and "c" represents a 2'-O-methylcytidine-5'-phosphate modified nucleotide base. There is a phosphorothioate bound in between the terminal 3' thymidines in SEQ ID NO:3. There is a phosphorothioate bound in between the terminal 5' thymidine and the cytidine, and a phosphorothioate bound in between the terminal 3' thymidines in SEQ ID NO:4. There is also a phosphorothioate bound in between the terminal 3' thymidines in SEQ ID NO:5. The iRNA agent can comprise an antisense strand comprising the nucleotide sequence of SEQ ID NO:4 or the nucleotide sequence of SEQ ID NO:5. The addition of the 5' deoxythymidine to the sense and antisense strands allows the activity and potency of the iRNA to be retained.

The iRNA agent can be coupled, e.g., covalently coupled, to a second agent. For example, an iRNA agent used to treat a particular neurological disorder can be coupled to a second therapeutic agent, e.g., an agent other than the iRNA agent. The second therapeutic agent can be one which is directed to the treatment of the same neurological disorder. For example, in the case of an iRNA used to treat a HD, the iRNA agent can be coupled to a second agent known to be useful for the treatment of HD. The iRNA agents described herein can be formulated for administration to a subject. Additionally, an iRNA preparation can be formulated in combination with another agent, e.g., another therapeutic agent or an agent that stabilizes an iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

The iRNA agent used in the methods of the present invention contains a detectable label that does not adversely affect the effectiveness of the labeled iRNA agent to decrease expression of the target RNA as compared to the labeled iRNA agent without the label, and does not adversely effect the distribution of the labeled iRNA agent in the brain as compared to the labeled iRNA agent without the label. Any detectable label for the iRNA agent can be used. For example, the label can be a radioisotope, such as carbon-11, carbon-14, fluorine-18, iodine-131, indium-111, and gadolinium. The methods of the invention also contemplate that the labeled iRNA is administered to the brain in a tracing composition.

It is contemplated that the label, such as carbon-14-labeled nucleoside, can be attached to the 5' terminus of the antisense strand via a phosphorothioate bond.

iRNA can be modified so that it can be labeled, such as by adding a DNA nucleotide to the 5' terminus of the antisense strand of the iRNA. For example, the 5' DNA nucleotide can be 5' deoxythymidine.

The iRNA agents can be in isolated form or can be part of a treatment composition used for the methods described herein, particularly as a treatment composition formulated for delivery to the brain of a mammal. The treatment compositions can contain one or more iRNA agents, or iRNA agents with modified nucleotides. The iRNA agents can also be incorporated into pharmaceutical compositions suitable for administration. For example, compositions can include one or more species of an iRNA agent and a pharmaceutically acceptable carrier. A pharmaceutically acceptable carrier can include any and all solvents, dispersion media, coatings, antibacterial and antifungal agents, isotonic and absorption delaying agents, and the like, compatible with pharmaceutical administration. Such carriers include, but are not limited to, saline, buffered saline, dextrose, water, glycerol, ethanol, and combinations thereof. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions useful according to the invention can also include encapsulated formulations to protect the iRNA agents against rapid elimination from the body, such as a controlled release formulation, including microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Delivery Systems and Methods

The solutions and compositions used in the present invention can be delivered to the brain by any known means. In one embodiment, the composition can be delivered by way of a catheter or other delivery device having one end implanted in a tissue, e.g., the brain by, for example, intracranial infusion. In some aspects, intracranial infusion is intrastriatal infusion, intraputamenal infusion, intracaudate infusion, intraventricular infusion, intraparenchymal infusion and intracortical infusion. In another aspect, a solution or composition is delivered to the CNS by intrathecal infusion.

An embodiment of the invention provides a system for determining and delivering to the brain of a mammal a solution or composition. The solution or composition may comprise one or more of an iRNA agent, a tracer, a therapeutic molecule or an imaging agent.

Referring to FIG. 13, one delivery system 15 useful with the methods of the invention for delivering a solution or composition is shown. Other systems useful for delivering solutions or compositions to the brain are described in US Published Application No. 2005/0048641. The system shown in FIG. 13 comprises a therapy delivery device 30. The device 30 comprises a pump 40 coupled to a reservoir 12 for housing a solution or composition. The system 15 further comprises a catheter 38. The catheter 38 comprises a proximal end 35 coupled to the pump 40 and a delivery region 39 adapted for delivering the composition or solution to a delivery location within the mammal. The catheter 38 can have one or more delivery regions 39 along the length of the catheter 38 and that a delivery region may or may not be at the distal end of the catheter 38. The therapy delivery device 30 can be implantable or may be an external device. The therapy delivery device 30 can have a port 34 into which a hypodermic needle can be inserted to inject a quantity of solution or composition into reservoir 12. The device 30 can further comprise a catheter port 37, to which the proximal end 35 of catheter 38 can be coupled. The catheter port 37 in this embodiment is operably coupled to pump 40. A connector 14 can be used to couple the catheter 38 to the catheter port 37 of the device 30. Device 30 can take the form of any pump system, including but not limited to, a drug reservoir and/or a drug pump of any kind, for example an osmotic pump, an infusion pump, an electromechanical pump, an electroosmotic pump, an effervescent pump, a hydraulic pump, a piezoelectric pump, an elastomeric pump, a vapor pressure pump, or an electrolytic pump. One example of a suitable pump is the device shown in U.S. Pat. No. 4,692,147 (Duggan), assigned to Medtronic, Inc., Minneapolis, Minn., an embodiment of which is commercially available as the Synchromed® infusion pump manufactured by Medtronic, Inc., the patent is incorporated herein by reference. Device 30 may also take the form of Medtronic's Synchromed® II infusion pump.

The therapy delivery device 30, such as Medtronic's SYNCHROMED or SYNCHROMED II pump systems, can be operated to discharge a predetermined dosage of the pumped fluid to a delivery location of a mammal. The therapy delivery device 30 can contain a microprocessor 42 or similar device that can be programmed to control the amount and/or rate of delivery of the composition or solution or programmed to change the concentration of a tracer, therapeutic composition or agent in the solution being delivered to the mammal. The programming can be accomplished with an external programmer/control unit (not shown) via telemetry. A controlled amount of a solution or composition comprising a therapeutic agent may be delivered over a specified time period. With the use of a therapy delivery device 30, different dosage regimens can be programmed for a particular mammal. A programmed therapeutic device 30 allows for starting conservatively with lower doses and adjusting to a more aggressive dosing scheme, if warranted, based on safety and efficacy factors. It may be desirable to reduce, rather than eliminate, the temporal or spatial expression of a targeted gene in which case a therapy delivery device 30 can allow for appropriate dose titration and distribution. Delivery device 30 can also allow for delivery of therapeutic agent to be stopped temporarily and resumed when desired. For example, delivery of agent can be stopped to perform diagnostic tests, intervene with a different therapy, or for safety reasons.

The device 30 can be implanted below the skin of a patient. Preferably, the device 30 is implanted in a location where the implantation interferes as little as practicable with activity of the mammal. The device 30 can be implanted subcutaneously in any medically acceptable area of the human body such as in a subcutaneous pocket located in the chest below the clavicle, in an abdominal subcutaneous pocket, in the patient's cranium, and the like.

In one embodiment, therapy delivery device 30 and delivery system 15 may take the form of a device and system described in U.S. Pat. No. 6,042,579, entitled "Techniques For Treating Neurodegenerative Disorders By Infusion Of Nerve Growth Factors Into The Brain", which patent is incorporated herein by reference in its entirety.

Referring to FIG. 14, the delivery system 15 may include a sensor 500. Sensor 500 may detect an event associated with an effect of the RNA inhibitory agent, the disease to be treated, the distribution of a therapeutic agent in the brain or other change in a delivery parameter. The sensor 500 may relay information regarding the detected event, in the form of a sensor signal, to processor 42 of device 30. The sensor 500 may be operably coupled to processor 42 in any manner. For example, the sensor 500 may be connected to processor via a direct electrical connection, such as through a wire or cable. Sensed information, whether processed or not, may be recoded by the device 30 and stored in memory (not shown). The stored sensed memory may be relayed to an external programmer, where a physician may modify one or more parameter associated with the therapy based on the relayed information. Alternatively, based on the sensed information, the micro processor 42 may adjust one or more parameters associated with delivery of a solution or composition. For example, the micro processor 42 may adjust the amount and timing of the infusion of such solution or composition. Any sensor 500 capable of detecting an event associated with an effect of the RNA inhibitory agent, the disease to be treated, the distribution of a therapeutic agent in the brain or other change in a delivery parameter may be used. Preferably, the sensor 500 is implantable. It will be understood that two or more sensors 500 may be employed.

In an embodiment, the sensor 500 may be a sensor as described in, e.g., U.S. Pat. No. 5,978,702, entitled "Techniques Of Treating Epilepsy By Brain Stimulation And Drug Infusion," which patent is hereby incorporated herein by reference in its entirety, or U.S. patent application Ser. No. 10/826,925, entitled "Collecting Sleep Quality Information Via A Medical Device," filed Apr. 15, 2004, which patent application is hereby incorporated herein by reference in its entirety.

Methods that use a catheter to deliver a therapeutic agent to the brain generally involve inserting the catheter into the brain and delivering the agent, solution or composition to the desired location. To accurately place the catheter and avoid unintended injury to the brain, surgeons typically use stereotactic apparatus/procedures. (U.S. Pat. No. 4,350,159) During a typical implantation procedure, an incision may be made in the scalp to expose the patient's skull. After forming a burr hole through the skull, the catheter may be inserted into the brain.

Other delivery devices useful with methods of this invention includes a device providing an access port, which can be implanted subcutaneously on the cranium through which therapeutic agents may be delivered to the brain, such as the model 8506 ICV Access Port and the 8507 Intraspinal Port, developed by Medtronic, Inc. of Minneapolis, Minn. Two models of catheters that can function with the model 8506 access port include the model 8770 ventricular catheter (Medtronic, Inc.), for delivery to the intracerebral ventricles, which is disclosed in U.S. Pat. No. 6,093,180, and the infusion catheter developed by Medtronic, Inc., for delivery to the brain tissue itself (i.e., intraparenchymal delivery), described in U.S. patent publications 2009/540,444 and 2009/625,751, the teachings of which are herein incorporated by reference. The latter catheter has multiple outlets on its distal end to deliver the therapeutic agent to multiple sites along the catheter path. Other systems provide catheter assemblies, systems, and methods operable to introduce an agent into the body while reducing the occurrence of backflow of the agent along the catheter assembly track. (U.S. patent publication 2009/143,764) Such catheter assemblies can be used in various applications including the treatment of acute and chronic medical conditions.

The striatum is a suitable area of the brain for delivery of an iRNA agent. Stereotactic maps and positioning devices are available and positioning can be effected by the use of anatomical maps obtained by CT and/or MRI imaging of the subject's brain to help guide the delivery device to the chosen target.

A therapeutic or prophylactic amount effective to treat a neurological disorder by the methods disclosed herein comprises a sufficient amount of the iRNA agent delivered during the entire course of treatment to ameliorate or reduce the symptoms of the neurological disorder being targeted for treatment. These iRNA agents can also contain a pharmaceutically acceptable carrier or excipient. Such carriers or excipients include any pharmaceutical agent that does not itself induce the production of antibodies harmful to the individual receiving the composition, and which may be administered without undue toxicity. Additionally, compositions for intracranial administration can include sterile aqueous solutions which can also contain buffers, diluents and other suitable additives.

The iRNA agents and therapeutic compositions of the invention are administered in dosages sufficient to inhibit expression of the gene of interest, for example, the htt gene. The methods of the invention contemplate that the concentration of the labeled iRNA agent in the tracing composition is in the range of 0.1 mg/mL to 50 mg/mL. In one embodiment, the concentration of labeled iRNA agent in the tracing composition is 0.5 mg/mL to 24 mg/mL. In another embodiment, the concentration of labeled iRNA agent in the tracing composition is 2 mg/mL to 12 mg/mL.

The iRNA agents and compositions can be administered by continuous delivery, intermittent delivery, or through a combination of continuous and intermittent delivery. In one embodiment, the tracing composition is continuously administered from 1 hour to 30 years. In other embodiments, the tracing composition is continuously administered from 6 hours to 20 years, or from 1 day to 35 days. In another embodiment, intermittent administration of the tracing composition comprises: two or more cycles of administration, wherein one cycle is 1 hour to 30 days of continuous administration followed by 1 day to 60 days with no administration; two or more cycles of administration, wherein one cycle is 6 hours to 10 days of continuous administration followed by 1 day to 60 days with no administration; two or more cycles of administration, wherein one cycle is 6 hours to 3 days of continuous administration followed by 3 days to 30 days with no administration; or two or more cycles of administration, wherein one cycle is 1 day to 3 days of continuous administration followed by 4 days to 21 days with no administration. The time for the cycle of administration after the no administration term can be the same as, shorter than, or longer than the time of the administration cycle before the no administration term.

The tracing composition can be administered continuously at a rate of 0.03 µl/min to 10 µl/min. In other embodiments, the tracing composition is administered continuously at a rate of 0.05 µl/min to 1.0 µl/min. In another embodiment, the concentration of the labeled iRNA agent in the composition is 4 mg/mL to 12 mg/mL and is administered continuously at a rate of 0.03 µL/min to 2.0 µL/min for 2 or more days.

In one embodiment, the iRNA agent inhibits Huntington protein by at least 20% within 4 mm from the site of administration. In another embodiment, the iRNA agent inhibits Huntington protein by at least 40% within 4 mm from the site of administration.

Many factors can influence the dosage and timing required to effectively treat a subject, including, but not limited to, the severity of the disease or disorder, previous treatments, the general health and/or age of the subject, and other diseases present. Moreover, treatment of a subject with an iRNA agent or a therapeutically effective amount of a composition can include a single treatment or a series of treatments. Estimates of effective dosages and in vivo half-lives for the individual iRNA agents encompassed by the invention can be made using conventional methodologies or on the basis of in vivo testing using an appropriate animal model. In addition, the label can dissociate from the iRNA agent at a measured rate. If that occurs, the calculation of the effective dosage can be corrected such that actual tissue concentration is calculated.

In addition to their administration individually or as a plurality, the iRNA agents of the invention can be administered in combination with other known agents effective in treatment of diseases. In any event, the administering physician can adjust the amount and timing of iRNA administration on the basis of results observed using standard measures of efficacy known in the art or described herein.

Diagnostic Method for Determining an Effective Amount of Treatment

The present invention provides treatment compositions and systems and methods for determining and delivering an effective amount of treatment composition for treating a central nervous system disorder in a mammal. Determining the effective amount of a treatment composition to be delivered to the CNS is desirable because if too little therapeutic agent is administered, the disease is not treated. If too much therapeutic agent is administered, the therapeutic is wasted, a consequence which is particularly undesirable when the therapeutic agent is expensive or difficult to obtain.

In the present methods, a tracing composition is administered, via a catheter, to the brain of a mammal. The tracing composition contains a detectably labeled iRNA agent with an antisense sequence that is substantially complementary to a target RNA, such that the labeled iRNA agent is capable of decreasing expression of the target RNA in the brain. The detectable label does not adversely affect the effectiveness of the labeled iRNA agent to decrease expression of the target RNA as compared to an iRNA agent without the label. Additionally, the detectable label that does not adversely affect the distribution of the labeled iRNA agent as compared to the labeled iRNA agent without the label. The labeled iRNA agent used in tracing composition can be any of the sequences detailed above.

When observing distribution of an infused drug to the brain, typically the drug distribution is referred to as the "Volume of Distribution" or $V_d$. The $V_d$ is a measure of the distribution of the label, and the sensitivity of the instrument to detect the label, rather than a measurement of where the drug is having an effect. Also of interest to researchers and clinicians is where the drug is having a meaningful physiological effect. This is the Volume of Efficacy, $V_e$, which is defined as the volume of the brain where the drug concentration is higher than the Effective Concentration ($c_e$). The $c_e$ can also be determined from any drug distribution imaging modality and its corresponding efficacy modality. For example, the $c_e$ can be determined using quantitative autoradiography (qARL) to image the distribution of the drug, and reverse transcriptase quantitative PCR (RT-qPCR) to measure efficacy, e.g. measurement of mRNA silencing after an infusion of iRNA.

Accordingly, a solution comprising a tracer is introduced via a catheter to the brain of a mammal, and the distribution of the solution during delivery is monitored by imaging the tracer in the solution to determine whether a target volume of distribution at steady state is substantially achieved.

If a target volume of distribution at steady state is not substantially achieved, the rate of delivery of the solution and/or the concentration of the tracer in the solution is modified until target volume of distribution at steady state is substantially achieved. The rate of delivery of the therapeutic composition and concentration of the therapeutic agent in the therapeutic concentration to substantially achieve the target volume of distribution at steady state can then be determined based on the rate of delivery and concentration of the tracer solution at which the target volume of distribution at steady state was substantially achieved. The therapeutic composition can then be delivered via a catheter to the brain of the mammal using the rate and concentration determined from the delivery of the solution containing the tracer.

The solution can be delivered by convection enhanced delivery (CED). CED of drugs directly into the parenchyma of the brain uses a continuous pressure gradient for distribution of drug into the interstitial space. The primary advantages of CED are circumvention of the blood-brain barrier by delivering drug directly to the extracellular space of the cells of interest, and the possibility of achieving broad distribution of drug with CED flow rates. To date, CED has been used clinically for administering drugs directly to the CNS to treat glioblastoma and Gaucher disease; however, there is potential for much broader applicability to treat neurological disorders, including neurodegenerative diseases such as Huntington's disease.

Monitoring the distribution of the solution and imaging the tracer through the brain tissue can be done by any imaging technique such as, for example, magnetic resonance imaging (MRI) or X-ray, e.g. positron emission topography (PET), and computed tomography (CT). If the tracer may be assumed to, or is known to have mobility in the brain tissue that is substantially similar to the therapeutic agent, delivery may be ceased when the tracer is observed to reach a target volume of distribution at steady state. Delivery may also be ceased before target volume of distribution at steady state is achieved by the tracer if it is expected or known that that the therapeutic agent has a greater mobility in the tissue than the tracer. For example, where a correlation has been established between the mobilities of the tracer and the therapeutic agent, delivery may be ceased when the observed distribution of the tracer corresponds to a desired distribution of the therapeutic agent.

If the tracer does not have a mobility that is substantially similar to the therapeutic agent, or cannot be assumed to have a substantially similar mobility as the therapeutic agent (for example, because the agent is highly toxic and delivery of the agent will damage sensitive tissues such as brain tissue outside of the target tissue) the volume of steady state distribution of the tracer that is observed may be converted to a volume of distribution of the therapeutic agent using a previously established correlation between the two. Thus, monitoring the volume of distribution for the tracer may be used to determine if the therapeutic agent has reached the target volume of distribution at steady state in the target tissue.

A tracer may comprise a metal chelate. A metal chelate is a complex of a metal ion and a metal chelating group (a group of atoms that serves to bind the metal ion). Examples of metal chelating groups include natural and synthetic amines, porphyrins, aminocarboxylic acids, iminocarboxylic acids, ethers, thiols, phenols, glycols and alcohols, polyamines, polyaminocarboxylic acids, polyiminocarboxylic acids, aminopolycarboxylic acids, iminopolycarboxylic acids, nitrilocarboxylic acids, dinitrilopolycarboxlic acids, polynitrilopolycarboxylic acids, ethylenediaminetetracetates, diethylenetriaminepenta or tetraacetates, polyethers, polythiols, cryptands, polyetherphenolates, polyetherthiols, ethers of thioglycols or alcohols, polyaminephenols, all either acyclic, macrocyclic, cyclic, macrobicyclic or polycyclic, or other similar ligands which produce stable metal chelates or cryprates (including sepulchrates, sacrophagines, and crown ethers). Specific examples of metal chelating groups include 1,4,7,10-tetraazacyclododecanetetraacetic acid (DOTA), 1,4, 7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tet-raazacyclotetradecanetetraacetic acid (TETA), DOTA-N(2-aminoethyl)amide and DOTA-N-(2-aminophenethyl)amide, BOPTA, HP-DO3A, DO3MA, DTPA, and various derivatives thereof. Additional examples are provided in Caravan et al., 1999, *Chem. Rev.*, 99:2293-2352 and in U.S. Pat. Nos. 5,246,692, 5,292,868 and 5,434,287. In one embodiment, the metal chelate is 2-(p-isothiocyanatobenzyl)-6-methyl diethylenetriamine pentaacetic acid (1B4M) chelates of gadolinium (III) ion.

Metals ions of the metal chelates may be paramagnetic ions if the imaging agent is to be used as a MRI contrast agent. Suitable metal ions include those having atomic numbers of 22-29 (inclusive), 42, 44 and 58-70 (inclusive) and have oxidation states of +2 or +3. Examples of such metal ions are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III).

If the macromolecular imaging agent is to be used as an X-ray contrast agent, the metal ion may be selected from the ions of W, Bi, Hg, Os, Pb, Zr, lanthanides, and combinations thereof. If a combined MRI/X-ray contrast agent is desired, the metal ion may be selected from the paramagnetic lanthanide ions. If a radiographic imaging agent is desired, the metal may be radioactive, such as the radioactive isotopes of In, Tc, Y, Re, Pb, Cu, Ga, Sm, Fe, or Co.

In other embodiments, the tracer comprises an iodinated CT contrast agent, such as iopanoic acid or iopamidol.

The tracer can be conjugated to a therapeutic agent. Although conjugation typically refers to formation of a covalent bond between the metal chelate and the therapeutic agent, other types of bonds (for example, ionic, dipole-dipole, or van der Waals) may suffice in some embodiments. The therapeutic agent of the present invention can include, but are not limited to, antisense oligonucleotides, ribozymes, iRNA, proteins, drugs, antibodies, antibody fragments, immunotoxins, chemical compounds, protein fragments and toxins.

Regardless of whether or not the tracer contains a therapeutic agent, the tracer is delivered in an amount sufficient to produce a target volume of distribution at steady state of the tracer solution determined by the image intensity of the tracer in the brain tissue. For example, if MRI is used to image the solution, the distribution of the tracer solution may be detected at some time after the imaging agent is administered. Monitoring the distribution of the solution can occur over a plurality of time intervals.

The present invention also contemplates methods of monitoring the effectiveness of a therapeutic composition containing a therapeutic agent delivered via a catheter to the brain of a mammal. This monitoring can occur after treatment with a therapeutic composition has started. The method can include the steps of: (a) after administering the therapeutic composition at a rate and concentration of the therapeutic agent in the composition to substantially achieve a target volume of distribution at steady state, (b) delivering a solution comprising a tracer via a catheter to the brain of a mammal to mimic the conditions at which the therapeutic composition was administered; and (c) monitoring distribution of the solution during delivery by imaging the tracer in the solution to determine whether a target volume of distribution at steady state is substantially achieved. Additional steps in the method can include: (d) if the target volume of distribution at steady state is not substantially achieved in step (c), modifying the rate of delivery of the solution or the concentration of the tracer in the solution or both, until the target volume of distribution at steady state is substantially achieved; (e) determining a rate of delivery of the therapeutic composition and a concentration of the therapeutic agent in the therapeutic concentration to substantially achieve the target volume of distribution at steady state based on the rate of delivery and concentration at which the tracer solution substantially achieved the target volume of distribution at steady state in step (c) or (d); and delivering the therapeutic composition at the rate determined in step (e) with the concentration of therapeutic agent in the therapeutic composition determined in step (e) via a catheter to the brain of the mammal. It is also contemplated that if the target volume of distribution at steady state is not achieved in step (c) or in step (d), then step (e) is performed at a predetermined rate and concentration of therapeutic agent.

EXAMPLES

Example 1

Synthesis of iRNA iRNA agents used in the present invention can be any RNA agent which can downregulate the expression of a target gene, such as an endogenous or pathogen target RNA. An iRNA agent can be a double stranded RNA duplex. The iRNA duplex has an antisense strand complementary to a nucleotide sequence of the target nucleic acid, and a sense strand sufficiently complementary to hybridize to the antisense strand.

An iRNA agent used in the methods of the invention contains a sense strand comprising SEQ ID NO:1 [5'GUCA-CAAAGAACCGUGCAGTT 3'] and an antisense strand comprising of SEQ ID NO:2 [5' CUGCACGGUUCUUU-GUGACTT 3']. Optionally, the iRNA agent can comprises 15 nucleotides or more nucleotides of SEQ ID NO:2. For example, the labeled iRNA agent comprises the nucleotide sequence of SEQ ID NO:2. The iRNA agents can be synthetically generated using methods well known in the art.

As has been experienced by those working in the antisense field, ribonucleic acids are often quickly degraded by a range of nucleases present in virtually all biological environments, e.g. endonucleases, exonucleases etc. This vulnerability may be circumvented by chemically modifying these oligonucleotides such that nucleases may no longer attack. Consequently, siRNAs can be synthesized with 2'-O-Methyl substitutions as previously described in U.S. Pat. No. 7,320,965.

The iRNA agent can comprise at least two chemically modified nucleotides. For example, the iRNA agent can comprise a sense strand consisting of SEQ ID NO:3 [5' GucA-cAAAGAAccGuGcAGTT 3'] and an antisense strand consisting of SEQ ID NO:4 [5' TCUGcACGGUUCUUUGUGACTT 3']; or the iRNA agent comprises a sense strand consisting of SEQ ID NO:3 [5' GucAcAAAGAAccGuGcAGTT 3'] and an antisense strand consisting of SEQ ID NO:5 [5' CUGcACGGUUCUUU-GUGACTT 3']. Capital letters represent unmodified nucleotide bases, the lower case letters represent 2'-O-methyl modifications. For example, "u" represents a 2'-O-methyluracil-5'-phosphate modified nucleotide base, and "c" represents a 2'-O-methylcytidine-5'-phosphate modified nucleotide base. There is a phosphorothioate bound in between the terminal 3' thymidines in SEQ ID NO:3. There is a phosphorothioate bound in between the terminal 5' thymidine and the cytidine, and a phosphorothioate bound in between the terminal 3' thymidines in SEQ ID NO:4. There is also a phosphorothioate bound in between the terminal 3' thymidines in SEQ ID NO:5. The iRNA agent can comprise an antisense strand comprising the nucleotide sequence of SEQ ID NO:4 or the nucleotide sequence of SEQ ID NO:5.

The iRNA agents can contain a carbon-14 label on the 5' terminus of the antisense strand. The carbon-14 labeled nucleoside can be connected to the RNA via a phosphorothioate bond.

Example 2

Cell Culture Studies dsRNA Suppresses Endogenous Human HD mRNA Expression in HeLa, Neuroscreen, and U87MG Cells Several siRNAs have been shown to be effective in suppressing huntingtin mRNA when transfected into HeLa cells (U.S. Pat. No. 7,320,965). One siRNA duplex (AD-5997, Alnylam Pharmaceuticals, Inc., Cambridge, Mass.) (SEQ ID NO:3 and SEQ ID NO:5) was particularly potent, inhibiting huntingtin mRNA levels by 86% and with an $IC_{50}$ value of 50 µM in HeLa cells. In addition to suppressing huntingtin mRNA, AD-5997 reduced endogenous Huntingtin protein levels in HeLa cells. The AD-5997 siRNA also inhibited endogenous HD mRNA expression in Neuroscreen cells (a PC12 sub-clone) (Cellomics, Pittsburgh, Pa.) and U87MG cells (American Type Culture Collection, Rockville, Md.). The $IC_{50}$ values were 6 nM in Neuroscreen cells and 2.7 nM in U87MG cells.

Absence of Immunostimulation with siRNA

To study the potential for immunostimulation by the siRNA molecules, IFN-α release was quantified after siRNA incubation with cultured human PBMCs; no immunostimulation was detected. Furthermore, the siRNAs were highly stable in cerebrospinal fluid (CSF).

14-Carbon Labeling Chemistry on siRNA Bioactivity and Stability In Vitro

Experiments were performed in vitro to assess the impact of modifications to the siRNA on the bioactivity of siRNA. HeLa cells were transfected with AD-5997 (SEQ ID NO:3 and SEQ ID NO:5) or AD-5997-dTs (SEQ ID NO:3 and SEQ ID NO: 4) at concentrations from 80 nM to 1.25 pM in 4 fold dilutions. Suppression of htt target mRNA was evaluated by bDNA to generate dose response curves and IC50's.

The suppression of the htt target mRNA with the addition of AD-5997 or AD-5997-dTs in vitro is shown in FIGS. 9A and 9B. In HeLa cells, the $IC_{50}$ of AD-5997 was calculated to be 1.04 nM, while the $IC_{50}$ of AD-5997-dTs was calculated to be 0.52 nM. Therefore, AD-5997-dTs siRNA showed similar potency and maximal effect as compared to AD-5997 siRNA in vitro.

FIG. 10 shows the amount of AD-5997 and AD-5997-dTs that can suppress the target mRNA in vitro. The figure demonstrates that AD-5997 and dTs modified AD-5997 have similar potency and maximal effect to suppress htt mRNA in vitro in HeLa cells, and that modifications (dTs on 5'-end of antisense strand) do not alter siRNA bioactivity in vitro.

Example 3

Rat Studies

In Vivo Down-Modulation of Endogenous HD mRNA Levels by CNS Administration of siRNAs Targeting HD in Rats In rats, 1.3 mg AD-5997 or phosphate-buffered saline (PBS, vehicle control) was administered by continuous intrastriatal infusion over 7 days (U.S. Pat. No. 7,320,965). Male Sprague-Dawley rats, approximately 250-300 g body weight, had a stereotaxic implantation of a 30-gauge infusion cannula (Plastics One, Roanok, Va.) such that unilateral injections were targeted to the center of the striatum (anteroposterior +0.7 mm, mediolateral +3.0 mm, relative to bregma; dorsoventral 5 mm, relative to skull surface). Mini-osmotic pumps (Medtronic, Inc.) were primed overnight according to the manufacturer's specifications, implanted subcutaneously, and connected via catheters to deliver PBS, 1.1 mM AD-5997 at 0.5 uL/hr over 7 days. Four rats were used per group. At the end of the 7 day infusion period, animals were sacrificed, brains were removed, and ipsilateral striata encompassing the infusion site were flash frozen. Tissue samples of about 5-30 mg each were homogenized by sonication (BANDELIN electronic GmbH & Co. KG, Berlin, Germany) in Tissue and Cell Lysis solution (Epicentre, Madison, Wis.) containing 84 µg/ml Proteinase K (Epicentre). Lysates were then stored at −80° C. For carrying out the branched DNA assay, frozen lysates were thawed at room temperature, and huntingtin and GAPDH mRNA were quantified using the Quantigene Explore Kit (Panomics Inc., Fremont, Calif.) according to the manufacturer's instructions. For each tissue sample, the ratio of huntingtin/GAPDH (normalized huntingtin mRNA level) was calculated as an average of four determinations. These ratios were then averaged to obtain a group (treatment) average. AD-5997 reduced the normalized huntingtin mRNA levels in striatal tissue by 34% relative to the PBS control group. In addition, AD-5997 reduced the normalized huntingtin mRNA levels in cortical tissue by 22%. These results demonstrate that siRNAs, after intrastriatal infusion, not only down-modulate huntingtin mRNA levels within the striatum, but also in the cortex, another major brain region where neuronal loss occurs in Huntington's disease and which is located further from the infusion site.

In another experiment, AD-5997 was intrastriatally infused into rats at concentrations of 2 mg/mL, 4 mg/mL, 8 mg/mL, or 15 mg/mL at an infusion rate of 2.5 µL/hr for 7 days. The rats were euthanized and tissue samples obtained. Branched DNA was performed on the tissue samples, and the results were normalized to a control group. The results demonstrate that at a dose rate of 2 mg/mL, AD-5997 reduced huntingtin mRNA levels in striatal tissue by 23% compared to the control group. At a dose rate of 4 mg/mL, AD-5997 reduced huntingtin mRNA levels by 30% compared to the control group. At a dose rate of 8 mg/mL, AD-5997 reduced huntingtin mRNA levels in striatal tissue by 40% compared to the control group. At a dose rate of 15 mg/mL, AD-5997 reduced the huntingtin mRNA levels in striatal tissue by 48% compared to the control group.

To evaluate in vivo distribution or activity, siRNAs were continuously infused for 3 to 10 days directly into the rat striatum using an Alzet osmotic pump. Huntingtin mRNA was quantified as above, and brain sections were processed for Cy3-siRNA for distribution studies. Dose-dependent and infusion duration-dependent reduction of huntingtin mRNA was demonstrated. Distribution studies with a Cy3-tagged siRNA revealed labeled cells of neuronal morphology in the striatum, cortex, substantia nigra and thalamus, as reported in U.S. 2008/0039415.

14-Carbon Labeling Chemistry on siRNA Bioactivity and Stability In Vivo

Experiments were performed in vivo to assess the impact of 14C-labelling chemistry on the bioactivity of siRNA. Male Sprague-Dawley rats, approximately 300-330 g body weight, were divided into three groups of 8 rats each.

Alzet osmotic pumps (model 2ML4) were used to deliver AD-5997 (15 mg/ml) (0.9 mg/day/rat), AD-5997-dTs (15 mg/ml) (0.9 mg/day/rat), or PBS for to the striatum for 7 days at a rate of 2.4 µL/hr. The stereotaxic coordinates were: Anteroposterior=+0.5 mm, mediolateral=+3.0 mm, and dorsoventral=−5 mm.

At the end of 7 days, the siRNA stability in rat CSF was assessed. The results indicate that AD-5997 and AD-5997-dTs have similar stability over 8 days at 37° C. in rat CSF. After 8 days, over 86% of the full-length sense and antisense strands of AD-5997 and over 90% of the full-length sense and antisense strands of AD-5997-dTs were recovered.

bDNA for Htt mRNA suppression was also performed with tissue from the ipsilateral striatum, at the infusion site and 1 mm anterior and posterior to infusion site. Bioanalytical assay for siRNA concentration in tissue was performed on tissue from the ipsilateral striatum, at the infusion site and 1 mm anterior and posterior to infusion site.

FIG. 11 shows that there was almost identical suppression of Htt mRNA after administration of AD-5997 or AD-5997-dTs. Therefore, AD-5997 and AD-5997-dTs siRNA have similar activity in vivo with respect to target mRNA suppression, and addition of a dTs on 5'-end of antisense strand does not alter siRNA bioactivity in vivo.

Example 4

Non-human Primate Studies

Convection-Enhanced Delivery of Drugs into the CNS: Confirmation of Distribution Using MRI Contrast Agent in Non-Human Primate Delivery and distribution of an MRI contrast agent was evaluated using convection-enhanced delivery (CED) was used with a catheter designed to prevent backflow. In the following experiments, gadopentetate dimeglumine was chronically infused into the non-human primate putamen for 7 days at various flow rates. Non-human primates were infused at a flow rate of 0.1 µL/min, (2 animals), 0.55 (2 animals) or 1.0 µL/min (2 animals). While the putamen was targeted for infusion because of its central role in Huntington's disease, any tissue of interest can be targeted. Gadopentetate dimeglumine distribution was measured by post-operative brain MRI at 1, 4, and 7 days to assess anatomical distribution and the volume of distribution as a function of the volume infused.

Figure 1:
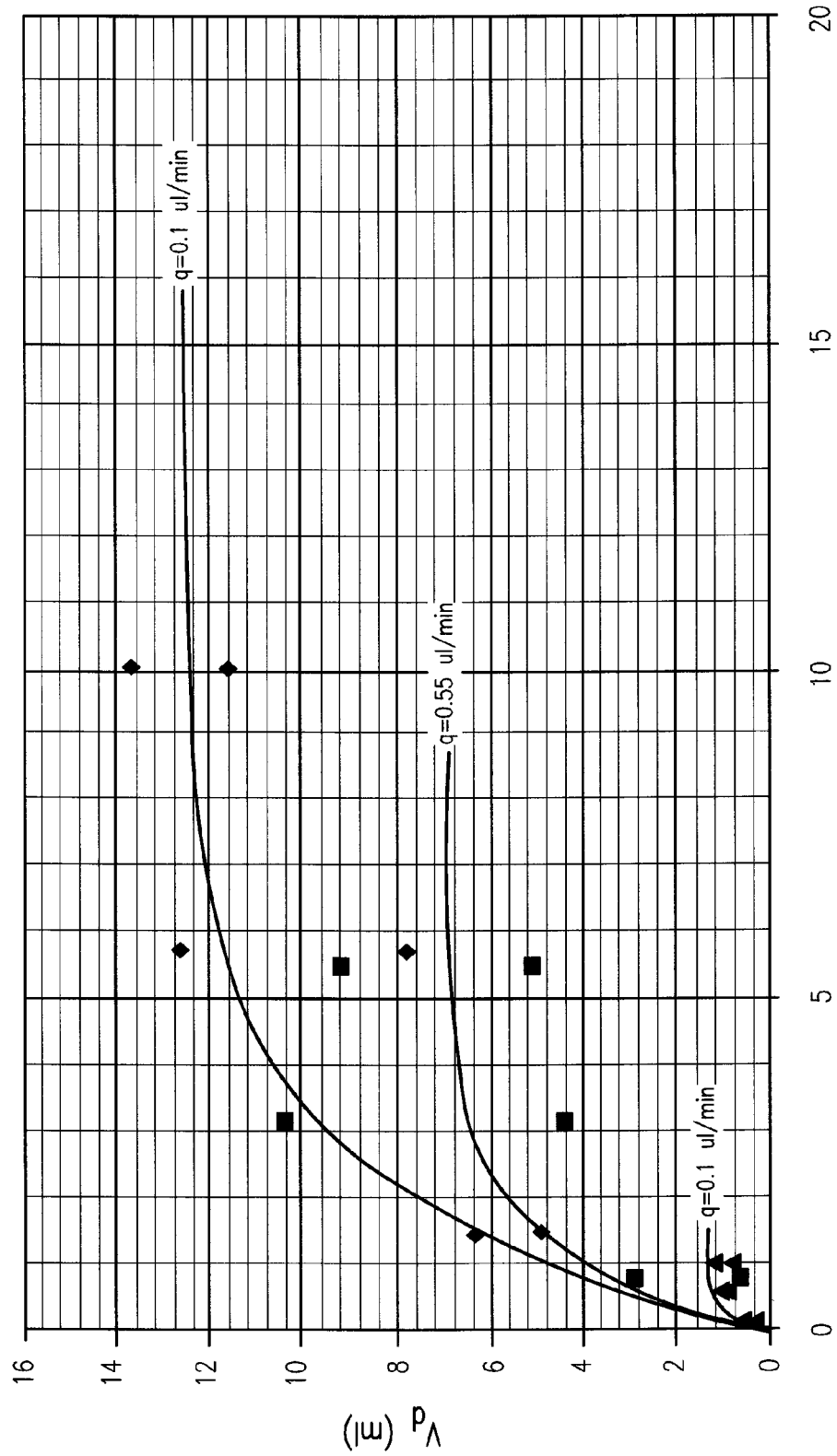
FIG. 1 depicts the volume of distribution of an MRI contrast agent versus volume of infusion for flow rates of 0.1 µL/min (triangles), 0.55 µL/min (squares), and 1.0 µL/min (diamonds) in the brains of non-human primates.
Figure 2:
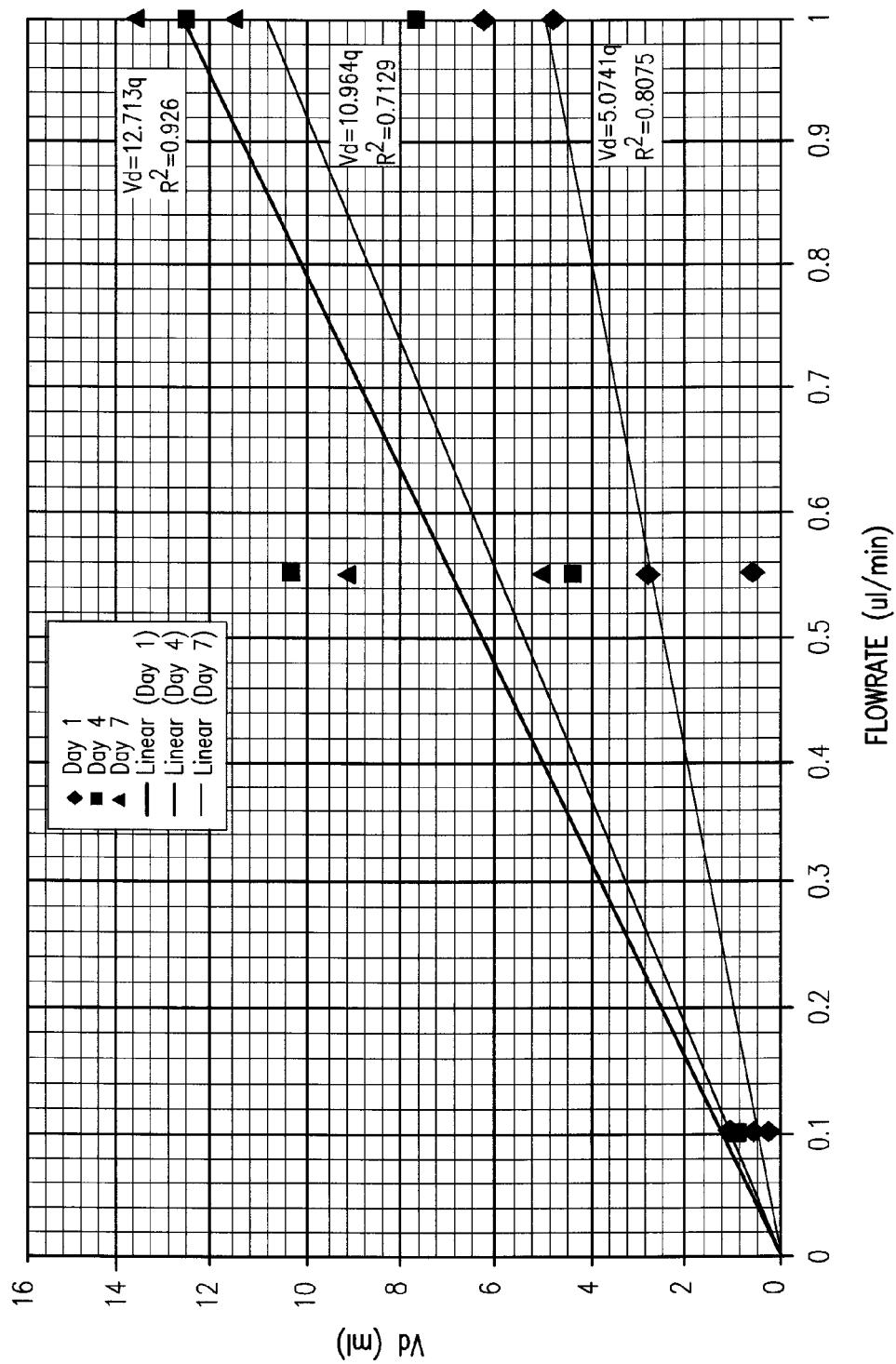
FIG. 2 depicts the volume of distribution of an MRI contrast agent versus the flow rate in the brains of non-human primates after 1, 4, or 7 days of infusion.
Figure 3:
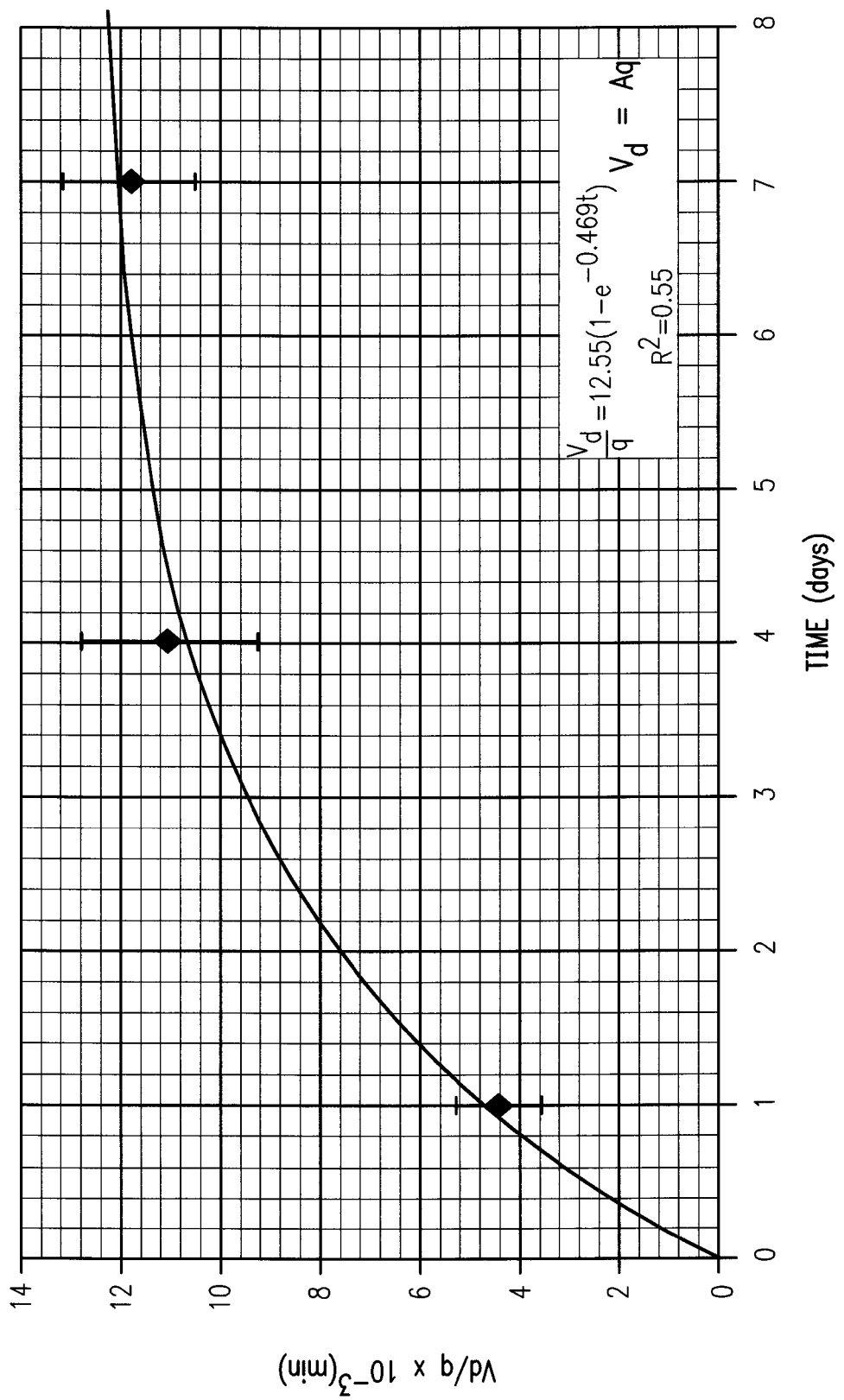
FIG. 3 shows a graph depicting the volume of distribution, normalized to flow rate, of an MRI contrast agent versus infusion time in the brains of non-human primates.

FIG. 1 shows the volume of distribution ($V_d$) versus the volume of infusion ($V_i$) over time for the three different flow rates. FIG. 2 shows the $V_d$ versus flow rate for the various time points, and the $V_d$ normalized to flow rate versus time for all of the animals over 1, 4, and 7 days are shown in FIG. 3. At higher flow rates (i.e. larger infused volumes), larger volumes of distribution within the brain were achieved with no backflow at CED infusion rates. In addition, the volume of distribution approached steady state values over time, indicating the presence of bulk flow clearance of the contrast agent from the parenchyma of the brain. Assuming that the steady state volume of distribution is a linear function of the flow rate, the ratio of these two values as a function of time was used to estimate the half-life of gadopentetate dimeglumine to be 36 hours.

These results demonstrate successful delivery into the brain at CED infusion rates with no significant backflow, indicating that this mode of administration has clinical utility for the treatment of neurodegenerative diseases. In particular, CED would be useful for the delivery of iRNA agents which target the huntingtin mRNA for the treatment of Huntington's disease. Gadopentetate dimeglumine and siRNA are similar because they are both hydrophilic, negatively charged, and have roughly the same particle size.

In addition, these results show the potential clinical utility of an MRI contrast agent for confirming infusate distribution of a composition in the brain intermittently after initial CNS delivery for chronic infusion. This surrogate distribution greatly aids the understanding of all drugs delivered chronically using CED and provides critical insight into chronic treatment of Huntington's disease with infused anti-htt siRNA.

Developing iRNA Therapeutics Targeting Huntingtin with Intraputamenal CNS Delivery: Non-Human Primate Studies CED was developed as method to deliver various pharmaceutical agents across the blood-brain barrier, providing a new modality for treating neurodegenerative disease and brain gliomas. A typical CED dosing paradigm involves the acute infusion of the agent to the parenchyma of the brain, after which the infusion hardware is removed. In order to develop a treatment for Huntington's disease, chronically implantable infusion hardware connected to the SynchroMed® II (Medtronic, Inc.) programmable pump and anchor/catheter hardware (Medtronic, Inc.) was created to deliver anti-huntingtin siRNA. In this therapeutic paradigm, the physiological effect of the iRNA is closely coupled to the distribution of the drug in the target anatomy.

Abdominally implanted programmable SynchroMed II® infusion pumps connected to catheters implanted in the brain were used to continuously infuse siRNA into the putamen of rhesus monkeys over 7 to 28 days. In order to determine the potential toxicity of AD-5997, the pumps were implanted into animals 7 days prior to AD-5997 administration and PBS was infused into the animals at a rate of 6 uL per day. AD-5997 was then administered by intraputamental infusion for 28 days to four groups of rhesus monkeys in amounts of 0 mg/mL (8 animals), 8 mg/mL (5 animals), 16 mg/mL (5 animals), or 24 mg/mL (8 animals). The infusion rate for all animals was 0.3 µL/min. The 28 day infusion period was followed by a 28 day recovery period. The animals were then euthanized.

The systemic effects of the siRNA were analyzed via blood chemistry, weight, neurological and clinical signs, plasma and CSF drug kinetics, and macro/micro pathology. Other than circumscribed tissue responses to infusion around the catheter, there were no apparent significant adverse clinical or histopathological effects from the siRNA treatment.

Seven days after the start of siRNA infusion, full-length siRNA was detected in the CSF by Attoprobe assay in the groups receiving AD-5997. (FIG. 4) No siRNA was detected in the plasma.

To determine the distribution of the siRNA as well as the ability of the siRNA to suppress target RNA, varying concentrations of AD-5997 siRNA radiolabeled with $^{14}C$-deoxythymidine (attached via a sulphur bond to 5' terminus of the antisense strand) (AD-3812, SEQ ID NO:3 and SEQ ID NO:4, Alnylam Pharmaceuticals, Inc.) and unlabeled AD-5997 siRNA were intraputamentally infused for 7 days into female rhesus monkeys. Groups were infused with: 4 mg/mL of AD-3812 at an infusion rate of 0.1 µL/minute (3 animals), 16 mg/mL of AD-3812 at an infusion rate of 0.1 µL/minute (3 animals), 4 mg/mL of AD-3812 at an infusion rate of 0.5 µL/minute (3 animals), 16 mg/mL of AD-3812 at an infusion rate of 0.5 µL/minute (3 animals), 8 mg/mL of AD-3812 at an infusion rate of 0.3 µL/minute (6 animals), or 12 mg/mL of AD-3812 at an infusion rate of 0.3 µL/minute (6 animals). PBS was used as a control.

Seven 2 mm thick brain slabs per monkey were obtained. Tissue punches were taken from each of the brain slabs, for a total of 71 punches per animal. The infusion point for each brain was identified with MRI and visual inspection of the slabs at necropsy. siRNA concentration and suppression distribution profiles were determined using RT-qPCR on tissue punches. The data exclusion criteria was as follows: the average of triplicate GADPH cycle threshold (Ct) values for any given sample cannot be greater than or equal to 100% of the average GAPDH Ct per plate, the % CV of the Ct triplicate cannot be greater than or equal to 1.0%, and the controls must contain a minimum of five replicates to be considered valid controls.

siRNA concentration and suppression distribution profiles were also determined using quantitative autoradiography (qARL) on coronal brain sections. With qARL, the absolute tissue concentration as a function of location in the brain can be determined. Two 40 μm sections per slab were used for qARL. The slices were organized spatially using Amira (Visage Imaging, San Diego, Calif.) and the volume encompassing the effective concentration ($c_e$) was calculated. 3D spatial reconstruction of sections taken for autoradiographic analysis enabled calculation of the volume of distribution. The resultant total mass retained (TMR) was calculated using qARL to establish a mass balance. It was found that the chronic TMR was much less than the siRNA total mass delivered (TMD), indicating the presence of an active clearance mechanism in the brain. Previous studies have shown that there is a movement of large molecules from the interstitial fluid to the perivascular spaces of the brain by bulk flow clearance. These data confirm bulk flow clearance hypothesis and indicate that there is a finite steady-state distribution and TMR for chronic CED drug infusions, wherein the ratio of TMR to the TMD trends to zero after a long period of time. These results demonstrate that an effective amount of a therapeutic agent can be determined and administered. This has important implications in the long-term treatment of Huntington's disease, particularly in the limited distribution of a targeted drug distribution in the anatomy of the human brain.

FIG. 5 depicts the maximum tissue concentration of AD-3812 after 7 days of intraputamenal infusion. The putamen (put) showed a higher maximum tissue concentration of AD-3812 than did the white matter (WM) after 7 days of infusion with 16 mg/mL of AD-3812 at a flow rate of 0.1 μL/min. In contrast, there was a similar maximum tissue concentration of AD-3812 between white matter and putamen with a flow rate of 0.5 μL/min. Therefore, the volume of distribution positively correlated with flow rate and concentration.

The results also demonstrated marked outline of the striatal structures. There were also instances where the adjacent white matter had a much higher concentration of labeled siRNA than the putamen. The white matter showed high anisotropy, which suggests that clearance from white matter is very slow and that the drug is accumulating at a rate faster than its removal. Additionally, the brain showed a strong outline on the outside of most sections, especially at high concentration/flow rate. This may be indicative of the movement of bulk flow clearance to the subarachnoid space. Finally, there appeared to be a small degree of labeled siRNA in the cortical regions after crossing over the white matter.

The mRNA suppression data were then co-registered with the corresponding tissue concentration as measured by qARL in order to calculate an effective concentration ($c_e$), defined as the tissue concentration of siRNA that yields a sufficiently high statistical and practical mRNA suppression for the drug distribution in the primate. In this case, target mRNA suppression was 45%. Statistical techniques were used to design orthogonal dosing paradigms wherein the input variables were chronic flow rate and $^{14}$C-siRNA concentration, and the measured output was the volume of efficacy ($V_e$) defined as the volume of brain occupied by a drug concentration at or above $c_e$. Regression analysis was performed to identify an empirical function relating $V_e$ to the flow rate and concentration of siRNA. This empirical function was of the form $V_e = A_0 + A_1*Q + A_2*c + A_3*Qc$, where q is the flow rate and c is the concentration; curvature was negligible in this instance and squared terms were removed. The constants are as follows: $A_o = -76.96$; $A_1 = -1073.53$; $A_2 = 3.64$ and $A_3 = 332.1$.

The tracer used to determine $c_e$ and $V_e$ oftentimes can be measured in $mg_{drug}/g_{tissue}$ per given qAR pixel. Each pixel represents a given volume (area of pixel×slice thickness), so multiplying the pixel volume with the associated tissue concentration (assuming 1 cm$^3 \approx 1$ $g_{tissue}$), and summing over all of the pixels gives the total mass that is present in the tissue at any particular time point. At SS, the amount of mass found in the parenchyma is not expected to increase.

The volume of efficacy for siRNA distribution after a 7 day infusion was similar to the volume of the rhesus putamen under certain infusion conditions. FIG. 6 depicts the $V_e$ in the putamen compared to the volume of the rhesus putamen. For example, in animal number 29 which received 16 mg/mL of AD-3812 at a flow rate of 0.1 μL/min, the total $V_e$ in the brain was 1310 μL, and the $V_e$ in the putamen was 480 μL. The highest siRNA concentration was detected in the putamen. FIG. 6 also demonstrates that siRNA can be distributed at or above $c_e$ to the rhesus monkey's entire putamen using one catheter at a higher concentration (16 mg/mL of AD-3812) and higher flow rate (0.5 μL/min). The $V_e$ determined in the rhesus brain can be used to predict drug distribution into the much larger human brain. Moreover, these data can be used as validation for the computational model predicting siRNA distribution in the human for clinical dosing paradigms. It is predicted that the $V_e$ of 16 mg/mL of AD-3812 with a flow rate of 0.5 μL/min would cover 24% of the human putamen. Since higher flow rates can be used in the human for clinical dosing, higher $V_e$ could be achieved with one catheter, resulting in siRNA being distributed at or above $c_e$ to greater than 24% of the human putamen.

There was a substantial suppression of htt mRNA throughout most of the putamen in the non-human primates after the 7 day infusion. FIG. 7 demonstrates that delivery of 8 mg/mL and 12 mg/mL of AD-3812 to the putamen suppressed htt mRNA 0-2 mm from the infusion site (FIG. 7A) as well as 4 mm away from the infusion site (FIG. 7B). Additionally, there was no significant difference in efficacy of htt mRNA suppression after infusion of 12 mg/mL of AD-3812 as compared to 8 mg/mL of AD-3812. The effective concentration of AD-3812 was determined to be 1.54 mg per gram of tissue.

While there was a substantial suppression of htt mRNA throughout most of the putamen after 7 days of infusion with 12 mg/mL and 8 mg/mL AD-3812, the sites anterior to the infusion site showed a higher level of htt mRNA suppression then did sites posterior to the infusion site. (FIG. 8) There was relatively consistent htt mRNA suppression from punch to punch within animals and within groups.

These results demonstrate that CED of htt siRNA to the non-human primate brain by continuous infusion is effective in suppressing htt mRNA and is well tolerated for at least one month.

In addition, htt protein suppression was evaluated in tissue punches from the 12 mg/mL 14C-htt siRNA group after 7 days of infusion at 0.3 uL/min. Tissue punches (A46, A50, A51, A41, A55 and A60) located within the putamen were evaluated for Htt and β-catenin by semi-quantitative Western blot analysis. Striatal lysate from the PBS group was used to generate a standard curve.

Suppression of Htt protein in tissue punches from non-human primate putamen corresponded qualitatively to mRNA changes. From animals that received CED of 12 mg/mL 14C-siHtt or PBS control at 0.3 μL/min, 1.2 mm diameter tissues punches in the putamen, located at a 4 mm distance from the infusion site, were obtained for semi-quantitative Western blot analysis. Tissue punches were homogenized in RIPA buffer (Sigma, St. Louis, Mo.) plus complete mini EDTA-free protease inhibitor cocktail (Roche Applied Science, Indianapolis, Ind.), and heated at 70° C. for 10 minutes. The standard curve was generated by loading 5, 10 or 15 μg of pooled samples from control animals treated with PBS. 10 μg of individual PBS or 14C-siHtt treated samples was loaded in each lane of a NuPAGE Novex 3-8% Tris-Acetate pre-cast gel (Invitrogen, Carlsbad, Calif.), run at 125V for 3 hours, then transferred to a nitrocellulose membrane at 35V for 2 hour. The membrane was blocked overnight at 4° C. in Odyssey blocking buffer (LI-COR, Lincoln, Nebr.). The blot was probed first with primary antibodies comprising mouse anti-Huntingtin (Millipore, Billerica, Mass.) at a dilution of 1:1000 and rabbit anti-β-catenin (Abcam, Cambridge, Mass.) at a dilution of 1:2000 diluted in LI-COR blocking buffer for 2 hour at room temperature. After washing with PBS plus 0.1% Tween 20, the blot was exposed to fluorescent-labeled secondary antibodies (anti-rabbit 680 nm and anti-mouse 800 nm from LI-COR Bioscience) at a dilution of 1:10,000 in Odyssey blocking buffer for one hour at room temperature. The blot was then washed four times with PBS plus 0.1% Tween 20 followed by one wash with 1×PBS. The LI-COR's Odyssey Infrared Imaging System was used to detect the protein bands. The expected sizes of Htt and β-catenin proteins, respectively, are 350 kDa and 92 kDa. The results show that CED of 12 mg/mL 14C-siHtt at 0.3 μL/min resulted in a reduction of Htt protein by 32% on average in tissue punches from the putamen, compared with a 44% average reduction of Htt mRNA in the putamen. (FIG. 12)

Immunohistochemistry of slabs of the non-human primate brain infused with Htt siRNA confirmed suppression of htt protein expression in the non-human primate brains when siRNA was infused for 28 days at 8 mg/ml and 0.3 μl/min. (Data not shown)

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A system for the treatment of Huntington's disease in a human, the system comprising a composition comprising an iRNA agent having an antisense strand comprising the nucleotide sequence of SEQ ID NOS: 2, 4 or 5 and a sense strand comprising the nucleotide sequence of SEQ ID NOS: 1 or 3, the composition having a concentration of the iRNA agent of 0.1 mg/ml to 50 mg/ml in a delivery device, and the delivery device is configured to administer the composition at a first flow rate of 0.3 μL/min to 2.0 μL/min followed by a second flow rate of 0.03 μL/min to 0.5 μL/min into the central nervous system (CNS).

2. The system according to claim 1, wherein the iRNA agent comprises an antisense strand comprising at least 15 nucleotides of SEQ ID NO: 2.

3. The system according to claim 1, wherein the iRNA agent comprises an antisense strand comprising the nucleotide sequence of SEQ ID NO: 2 and a sense strand comprising the nucleotide sequence of SEQ ID NO: 1.

4. The system according to claim 1, wherein the iRNA agent comprises at least two chemically modified nucleotides.

5. The system according to claim 1, wherein the iRNA agent comprises an antisense strand comprising the nucleotide sequence of SEQ ID NO: 4 and a sense strand comprising the nucleotide sequence of SEQ ID NO: 3.

6. The system according to claim 1, wherein the concentration of the iRNA agent in the composition is 0.5 mg/mL to 24 mg/mL.

7. The system according to claim 6, wherein the concentration of the iRNA agent in the composition is 2 mg/mL to 12 mg/mL.

8. The system according to claim 1, wherein the administration is intermittent and comprises two or more cycles of administration, wherein one cycle is 1 hour to 30 days of continuous administration at the first flow rate followed by 1 day to 60 days at the second flow rate that is slower than the first flow rate.

9. The system according to claim 1, wherein the administration is intermittent and comprises two or more cycles of administration, wherein one cycle is 6 hours to 10 days of continuous administration at the first flow rate followed by 1 day to 60 days at the second flow rate that is slower than the first flow rate.

10. The system according to claim 1, wherein the administration is intermittent and comprises two or more cycles of administration, wherein one cycle is 6 hours to 3 days of continuous administration at the first flow rate followed by 3 days to 30 days at the second flow rate that is slower than the first flow rate.

11. The system according to claim 1, wherein the administration is intermittent and comprises two or more cycles of administration, wherein one cycle is 1 to 3 days of continuous administration at the first flow rate followed by 4 days to 21 days at the second flow rate that is slower than the first flow rate.

12. The system according to claim 1, wherein the composition is administered to neural cells.

13. The system according to claim 12, wherein the neural cells are selected from the group comprising cortical cells, striatal cells, substantia nigra cells and thalamus cells.

14. The system according to claim 13, wherein the striatal cells are selected from the group comprising putamen cells and caudate cells.

15. The system according to claim 1 or 4, wherein the concentration of the iRNA agent in the composition is 4 mg/mL to 12 mg/mL.

16. The system according to claim 1, wherein the first rate is 0.5 μL/min and the second rate is 0.1 μL/min.

17. The system according to claim 1, wherein the antisense sequence is substantially complementary to a Huntington RNA such that the iRNA agent decreases protein expression by the Huntington RNA in the brain.

18. The system according to claim 1, wherein the composition is administered in a pharmaceutically acceptable carrier.

* * * * *